(12) United States Patent
Kasaini

(10) Patent No.: US 11,091,819 B2
(45) Date of Patent: Aug. 17, 2021

(54) EXTRACTION OF METALS FROM METALLIC COMPOUNDS

(71) Applicant: Rare Element Resources Ltd., Lakewood, CO (US)

(72) Inventor: Henry Kasaini, Littleton, CO (US)

(73) Assignee: Rare Element Resources Ltd., Littleton, CO (US)

( * ) Notice: Subject to any disclaimer, the term of this patent is extended or adjusted under 35 U.S.C. 154(b) by 530 days.

(21) Appl. No.: 14/831,020

(22) Filed: Aug. 20, 2015

(65) Prior Publication Data
US 2015/0354026 A1    Dec. 10, 2015

Related U.S. Application Data

(62) Division of application No. 14/158,824, filed on Jan. 18, 2014.
(Continued)

(51) Int. Cl.
*C22B 59/00*   (2006.01)
*C22B 3/46*    (2006.01)
(Continued)

(52) U.S. Cl.
CPC ........ *C22B 60/0291* (2013.01); *C07C 51/418* (2013.01); *C22B 3/10* (2013.01);
(Continued)

(58) Field of Classification Search
CPC ........ C22B 60/0291; C22B 3/10; C22B 3/46; C22B 59/00; C07C 51/418
(Continued)

(56) References Cited

U.S. PATENT DOCUMENTS 2,327,992 A    8/1943  Blumenfeld
2,815,262 A   12/1957  Bridger et al.
(Continued)

FOREIGN PATENT DOCUMENTS

CA    2868323 A1   10/2013
CN   101633516     1/2010
(Continued)

OTHER PUBLICATIONS

Notification of Transmittal of the International Search Report and the Written Opinion of the International Searching Authority for PCT/US2015/034986; dated Oct. 1, 2015; 9 pages.
(Continued)

*Primary Examiner* — Melissa S Swain
(74) *Attorney, Agent, or Firm* — David F. Dockery; The Navitas Intellectual Property Group LLC

(57) ABSTRACT

Methods for the extraction of metals such as rare earth metals and thorium from metal compounds and solutions. The methods may include the selective precipitation of rare earth elements from pregnant liquor solutions as rare earth oxalates. The rare earth oxalates are converted to rare earth carbonates in a metathesis reaction before being digested in an acid and treated for the extraction of thorium. A two-step extraction method may be applied to precipitate thorium as thorium hydroxide under controlled pH conditions such that pure thorium precipitate is recovered from a first step and a thorium-free rare earth solution is recovered at the subsequent step. The resulting rare earth solutions are of extremely high purity and may be processed directly in a solvent extraction circuit for the separation of rare earth elements, or may be processed for the direct production of a 99.9% bulk rare earth hydroxide/oxide concentrate.

19 Claims, 11 Drawing Sheets

Related U.S. Application Data

(60) Provisional application No. 61/754,420, filed on Jan. 18, 2013, provisional application No. 61/902,579, filed on Nov. 11, 2013.

(51) Int. Cl.

| | | |
|---|---|---|
| *C22B 3/44* | (2006.01) | |
| *C22B 60/02* | (2006.01) | |
| *C22B 3/10* | (2006.01) | |
| *C07C 51/41* | (2006.01) | |

(52) U.S. Cl.
CPC .................. *C22B 3/44* (2013.01); *C22B 3/46* (2013.01); *C22B 59/00* (2013.01); *C22B 60/02* (2013.01); *Y02P 10/20* (2015.11); *Y02P 20/582* (2015.11)

(58) Field of Classification Search
USPC .................................................. 423/21.1, 18
See application file for complete search history.

(56) References Cited

U.S. PATENT DOCUMENTS

| | | | |
|---|---|---|---|
| 2,815,264 A | 12/1957 | Calkins et al. | |
| 2,849,286 A | 8/1958 | Welt et al. | |
| 2,897,046 A | 7/1959 | Bohlmann et al. | |
| 2,901,496 A | 8/1959 | Cowan | |
| 2,902,338 A | 9/1959 | Bane | |
| 2,955,913 A | 10/1960 | Peppard et al. | |
| 2,988,421 A | 6/1961 | Kemp et al. | |
| 3,087,948 A | 4/1963 | Carter et al. | |
| 3,111,375 A | 11/1963 | Gottdenker et al. | |
| 3,112,990 A | 12/1963 | Krumholz et al. | |
| 3,159,452 A | 12/1964 | Lerner | |
| 3,378,352 A | 4/1968 | Hansen et al. | |
| 3,411,883 A | 11/1968 | Smit | |
| 3,434,809 A | 3/1969 | Swanson | |
| 3,582,264 A | 6/1971 | Chiola et al. | |
| 3,594,117 A | 7/1971 | Chiola et al. | |
| 3,635,658 A | 1/1972 | Ferri et al. | |
| 3,647,361 A | 3/1972 | Coltrinar et al. | |
| 3,740,199 A | 6/1973 | Gammill et al. | |
| 3,812,233 A | 5/1974 | Duncan | |
| 3,825,649 A | 7/1974 | Gresky et al. | |
| 3,835,213 A | 9/1974 | Ritcey et al. | |
| 4,265,862 A | 5/1981 | White et al. | |
| 4,285,830 A | 8/1981 | Muller | |
| 4,409,157 A | 10/1983 | Haas et al. | |
| 4,417,965 A | 11/1983 | Inoue | |
| 4,438,078 A * | 3/1984 | Nalewajek .......... C01F 17/0043 423/21.5 | |
| 4,439,326 A | 3/1984 | Heilgeist | |
| 4,461,748 A | 7/1984 | Sabot et al. | |
| 4,765,909 A | 8/1988 | Rourke et al. | |
| 4,804,649 A | 2/1989 | Sherif | |
| 4,973,455 A | 11/1990 | Tilley et al. | |
| 4,976,939 A | 12/1990 | Fabre et al. | |
| 5,011,665 A | 4/1991 | Cailly et al. | |
| 5,045,289 A | 9/1991 | Fernando et al. | |
| 5,192,443 A | 3/1993 | Delloye et al. | |
| 5,811,573 A * | 9/1998 | Nishihira ................ C07C 67/03 560/146 | |
| 6,293,973 B1 | 9/2001 | Farquharson et al. | |
| 7,993,612 B2 | 8/2011 | Mackowski et al. | |
| 8,263,028 B1 | 9/2012 | Vierheilig | |
| 2003/0215378 A1 | 11/2003 | Zhou et al. | |
| 2011/0182786 A1 | 7/2011 | Burba, III | |
| 2012/0156116 A1* | 6/2012 | Gao .......................... C22B 3/44 423/21.1 | |
| 2012/0207656 A1* | 8/2012 | Duyvesteyn .............. C22B 1/04 423/21.1 | |
| 2013/0283977 A1* | 10/2013 | Lakshmanan ........... C22B 59/00 75/743 | |

FOREIGN PATENT DOCUMENTS

| | | |
|---|---|---|
| CN | 103395820 | 11/2013 |
| EP | 2578538 | 4/2013 |
| JP | 62191422 | 8/1987 |
| JP | 2001010815 A | 1/2001 |
| RU | 2148019 C1 | 4/2000 |
| RU | 2249266 | 3/2005 |
| RU | 2484018 C2 | 6/2013 |
| WO | WO2012149642 | 11/2012 |

OTHER PUBLICATIONS

Office Action dated Dec. 5, 2018 for European Patent Application No. 14740863.7.
Rabie et al., "Monazite-Uranium Separation and Purification Applying Oxalic-Nitrate-TBP Extraction," Arab Journal of Nuclear Science and Applications, vol. 46(1), pp. 30-42 (2013).
Abreu et al., "Purification of Rare Earth Elements from Monazite Sulphuric Acid Leach Liquor and the Production of High Purity Ceric Oxide," Minerals Engineering, vol. 23, pp. 536-540 (2010).
Liao et al., "Clean Separation Technologies of Rare Earth Resources in China," Journal of Rare Earths, vol. 31, No. 4, pp. 331-336 (Apr. 2013).
Ball, "Extraction of Rare Earths from Monazite Sand Rare Earth Residues," Master's Thesis, University of British Columbia (1927).
Haxel, "Ultrapotassic Mafic Dikes and Rare Earth Element-and Barium-Rich Carbonatite at Mountain Pass, Mojave Desert, Southern California: Summary and Field Trip Localities," U.S. Geological Survey Report 2005-1219 (2005).
International Preliminary Report on Patentability for PCT/US14/12153, dated Jan. 29, 2015.
European Search Report dated May 24, 2017 for European Patent Application No. 14740863.7.
Office Action dated Jun. 5, 2017 for Canadian Patent Application No. 2,898,612.
International Search Report and Written Opinion dated Jun. 10, 2014 for International Application No. PCT/US2014/012153.
International Preliminary Report on Patentability dated Oct. 15, 2015 for International Application No. PCT/US2014/012153.
International Preliminary Report on Patentability dated Dec. 22, 2016 for International Application No. PCT/US2015/034986.
Office Action dated Sep. 27, 2017 for U.S. Appl. No. 14/735,118.
Office Action dated Oct. 18, 2017 for Australian Patent Application No. 2014207355.
Office Action dated Oct. 23, 2017 for Russian Patent Application No. 2015134576.
Office Action dated Jan. 18, 2018 for Canadian Patent Application No. 2,898,612.
Decision dated Feb. 12, 2018 for Russian Patent Application No. 2015134576.
Office Action dated Jan. 30, 2015 for U.S. Appl. No. 14/158,824.
Final Office Action dated Oct. 29, 2015 for U.S. Appl. No. 14/158,824.

* cited by examiner

EXTRACTION OF METALS FROM METALLIC COMPOUNDS

CROSS-REFERENCE TO RELATED APPLICATIONS

This application is a divisional application that claims the priority benefit of U.S. patent application Ser. No. 14/158,824, filed Jan. 18, 2014, which claims the priority benefit under 35 USC § 119 of U.S. Provisional Application No. 61/754,420 filed on Jan. 18, 2013, and claims the priority benefit under 35 USC § 119 of U.S. Provisional Application No. 61/902,579 filed Nov. 11, 2013. The disclosure of each of these applications is incorporated herein by reference in its entirety.

FIELD

This disclosure relates to the field of extractive metallurgy, such as for the extraction of rare earth metals and/or thorium from feedstocks containing these elements.

BACKGROUND

Rare earth elements (REEs) comprise seventeen elements in the periodic table, specifically the 15 lanthanide elements plus scandium and yttrium. REEs are a group of metallic elements with unique chemical, catalytic, magnetic, metallurgical and phosphorescent properties, and as such find use in a wide variety of modern devices including high-strength magnets, batteries, displays, lighting, and high performance metal alloys.

REEs are relatively plentiful in the earth's crust. However, REEs are typically highly dispersed and are not often found as concentrated rare earth minerals in economically exploitable ore deposits. The extraction of REEs from mineral deposits is also challenging because mineral deposits containing REEs typically also contain appreciable levels of radioactive elements such as thorium (Th) and uranium (U) that must be safely separated from the REEs during processing of the ore.

Other ore deposits, such as those containing tantalum (Ta) and/or niobium (Nb), may also contain appreciable amounts of thorium that must be safely removed from the metals during processing of the ore.

SUMMARY

It is one objective to provide a method for the selective extraction of rare earth elements from base metals by precipitation of pregnant liquor solutions to form rare earth oxalates. The rare earth oxalates may be converted to rare earth carbonates in a metathesis reaction before being digested in an acid and treated for the extraction of thorium.

It is also an objective to provide a method for the extraction of thorium by precipitating the thorium as thorium hydroxide under controlled pH conditions so that the thorium precipitates without precipitating substantial amounts of rare earth metals. The resulting rare earth solutions are of extremely high purity and may be processed in a solvent extraction circuit for the recovery of high purity rare earth metals, or may be treated to convert the solutions to rare earth oxides.

DESCRIPTION OF THE EMBODIMENTS

Figure 1:
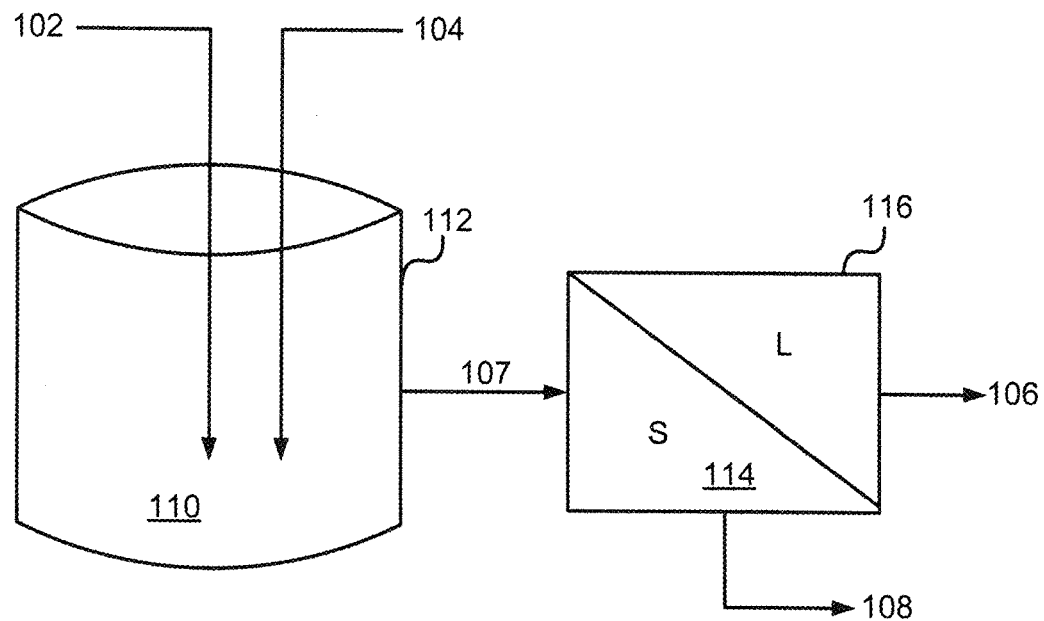
FIG. 1 is a schematic flowsheet illustrating a method for the selective precipitation of thorium as thorium hydroxide from an acidic solution.

In some embodiments, the present disclosure relates to methods for the selective precipitation of thorium (Th) from acidic solutions of metals, such as acidic solutions containing rare earth elements ("REEs"), such as an acidic solution that is derived from a pregnant liquor solution ("PLS") formed by acid leaching of an ore (e.g., a mineral ore concentrate) containing the REEs. In some embodiments, the present disclosure relates to methods for preparing the acidic solutions, such as from rare earth oxalates (REE-oxalates) or other rare earth compounds, which may be derived from a mineral ore. In some embodiments, the present disclosure relates to methods for the precipitation of REEs from a solution (e.g., a PLS) in the form of REE-oxalates. In other embodiments, the present disclosure relates to unique products that may be formed by the disclosed methods when applied alone or in combination.

REEs comprise 17 elements in the periodic table, namely the 15 lanthanide elements plus scandium and yttrium. Specifically, the REEs include scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). All of these REEs except Pm are found in nature, e.g., in mineral deposits. Many REEs find use in modern devices and have a very high value do to their relative scarcity. Of particularly high value are the REEs yttrium, praseodymium, neodymium, europium, terbium and dysprosium.

Many mineral deposits containing REEs also contain radioactive elements, such as thorium and uranium. Radioactive elements may also be found with other non-REE mineral deposits, such as uranium deposits, tantalum deposits and niobium deposits. It is highly desirable to separate these radioactive elements from the non-radioactive metals before final processing to extract the non-radioactive metals, e.g., from a solution of the non-radioactive metals.

In a first embodiment, a method for the selective precipitation of thorium from an acidic solution containing solubilized thorium is provided. The method may be applicable to solutions that contain other solubilized metals in addition to the thorium, such as solubilized REEs, uranium, tantalum or niobium. In one example, the acidic solution includes significant amounts of solubilized REEs (i.e., an acidic REE solution), such as an acidic solution that is derived from a rare earth ore concentrate. In one particular example, the acidic solution includes one or more of yttrium, praseodymium, neodymium, europium, terbium and dysprosium. Although the following description primarily describes the extraction of thorium from such acidic REE solutions, the thorium precipitation method of this embodiment may be applicable to other acidic solutions containing solubilized thorium, such as acidic solutions containing Group 5 metals such as tantalum and/or niobium.

The method of this embodiment includes the precipitation of thorium in the form of thorium hydroxide (e.g., $Th(OH)_3$ or $ThO(OH)_3$) from an acidic solution. For example, the method may include precipitating thorium as thorium hydroxide by contacting the acidic solution with a hydroxide precipitant, e.g., by contacting the acidic solution with a compound that includes a hydroxide group, such as sodium hydroxide (NaOH) and/or ammonium hydroxide ($NH_4OH$). Thorium hydroxide may be precipitated from the acidic solution while maintaining a substantial portion of other valuable metals (e.g., REEs) in solution for subsequent recovery of the other metals, such as in a solvent extraction circuit. In one example, the acidic solution may have a relatively low free acid content, such as about 5 g/l (grams per liter) of acid.

FIG. 1 illustrates a schematic flowsheet of a method for the precipitation of thorium from an acidic solution according to this embodiment. As illustrated in FIG. 1, an acidic solution 102 containing at least solubilized thorium is contacted with a hydroxide precipitant 104 in a hydroxylation step 110, e.g., by contacting the acidic solution 102 and the hydroxide precipitant 104 in a reactor 112 to cause thorium in the acidic solution 102 to precipitate as thorium hydroxide. After at least a portion of thorium in the acidic solution 102 has precipitated from the acidic solution 102 as thorium hydroxide, a thorium depleted solution 106 may be separated from a thorium hydroxide product 108 in a separating step 114, e.g., using a filter 116.

The acidic solution 102 contains at least solubilized thorium. As is discussed in more detail below, the acidic solution 102 may be derived from the leaching of a mineral ore (e.g., an ore concentrate) containing REEs or other high-value metals. Thorium is among the elements that are commonly found in mineral deposits containing REEs and the resulting acidic leach solutions typically contain undesirable concentrations of thorium. In one example of this embodiment, the concentration of solubilized thorium in the acidic solution 102 is at least about 50 mg/l (milligrams per liter), such as at least about 100 mg/l of solubilized thorium in the acidic solution 102, or even at least about 200 mg/l of solubilized thorium.

The acidic solution 102 may also include one or more REEs, i.e., REEs that are also solubilized in the acidic solution 102. For example, the acidic solution 102 may include REEs in a concentration of at least about 10 grams per liter (g/l). In certain characterizations, the acidic solution 102 includes a relatively high concentration of REEs, such as at least about 15 g/l REEs, at least about 20 g/l REEs, at least about 30 g/l or even at least about 50 g/l REEs, where the REEs are solubilized (e.g., dissolved) into the acidic solution 102. Typically, the acidic solution 102 will include not greater than about 100 g/l REEs. In one particular characterization of this example, the acidic solution 102 includes at least one or more REEs of particularly high value, such as one or more of praseodymium, neodymium, europium, terbium and dysprosium.

The solution 102 is acidic and may have a pH of not greater than about pH 3.8, such as not greater than about pH 4.2, prior to being contacted with the hydroxide precipitant 104. In one example, the acidic solution includes nitric acid ($HNO_3$), although other acids such as sulfuric acid ($H_2SO_4$) may also be useful in the embodiments disclosed herein. For example, the acidic solution 102 may comprise nitric acid ($HNO_3$) and may be obtained from the acid digestion of rare earth compounds, e.g., the acid digestion of earth oxide (RE-oxides), rare earth hydroxides (RE-hydroxides), rare earth oxalates (RE-oxalates) and/or rare earth carbonates (RE-carbonates) with nitric acid to form solubilized nitrate compounds of REEs. Nitric acid is particularly useful, as the thorium hydroxide precipitated during hydroxylation 110 will becomes stable and thus will not dissolve, even at a relatively low pH.

The acidic solution 102 comprises nitric acid, and in one particular example, the acidic solution 102 has a free acid concentration in the range of from about 0.5 g/l to about 55 g/l $HNO_3$. When the acidic solution 102 comprises nitric acid, the solubilized elements (e.g., thorium and REEs) may be in the form of solubilized nitrate salts. It is an advantage of this embodiment that the acidic solution 102 may have a relatively low free acid concentration, and therefore may require relatively small quantities of the hydroxide precipitant 104 to precipitate thorium hydroxide and to avoid diluting metal species in solution, which favors crystallization to precipitate thorium.

The acidic solution 102 may also include traces of non-REE elements that are solubilized in the acidic solution 102. For example, the non-REE elements may include metallic elements, such as: alkali metals such as sodium (Na) and potassium (K); alkaline earth metals such as magnesium (Mg), calcium (Ca), strontium (Sr) and barium (Ba); transition metals such as nickel (Ni), copper (Cu), zirconium (Zr), iron (Fe), manganese (Mn) and titanium (Ti); post-transition metals such as lead (Pb) and aluminum (Al); metalloids such as silicon (Si); and radioactive metals (e.g., actinides) such as thorium (Th) and uranium (U). The non-REE elements may also include non-metallic elements such as sulfur (S) and phosphorous (P).

In one example, however, the acidic solution 102 includes primarily REEs and thorium, with little or no other non-REE elements (e.g., base metals) that are solubilized in the acidic solution 102. For example, the acidic solution 102 may comprise not greater than about 5 wt. % non-REE elements, such as not greater than about 3 wt. % non-REE elements. Method for the formation of such acidic solutions are described in more detail below.

The hydroxylation step 110 includes contacting the acidic solution 102 with a hydroxide precipitant 104, such as sodium hydroxide or ammonium hydroxide, to precipitate a thorium hydroxide product 108 (e.g., predominately containing particulate thorium hydroxide). For example, the reactants may be contacted in a reactor 112 under conditions such that at least a portion of the thorium solubilized in the acidic solution 102 precipitates as a thorium hydroxide product 108.

It is an advantage of the method of this embodiment that the thorium may be precipitated from the acidic solution 102, while a substantial majority of the REEs contained in the acidic solution 102 remain solubilized in a thorium depleted solution 106 that is separated from the thorium hydroxide product 108. To ensure that sufficient quantities of thorium precipitate from the acidic solution 102 and that a substantial majority of REEs in the acidic solution 102 remains solubilized, it has been found that the pH during the hydroxylation step 110 should be maintained at a pH that enables high selectively for thorium, i.e., to preferentially precipitate thorium from the acidic solution 102. In one characterization, the pH during the hydroxylation step 110 is within the range of at least about pH 3 and not greater than about pH 4. It has been found that increasing the pH within this range may increase the amount of thorium precipitated from the acidic solution 102 as a thorium hydroxide product 108. In one characterization, the pH during the hydroxylation step 110 is maintained at a pH of at least about pH 3.0, such as at least about pH 3.1, at least about pH 3.2, at least about pH 3.3, at least about pH 3.4 or even at least about pH 3.5, such a at least about pH 3.6. However, as the pH approaches about pH 4, an increasing quantity of REEs may also precipitate from the acidic solution 102 (e.g., as particulate REE-hydroxides). In the embodiment illustrated in FIG. 1, to avoid the precipitation of undesirable quantities of REEs from the solution, the pH should be maintained at less than ph 4, such as not greater than pH 3.9 or not greater than pH 3.8. In one example, the pH during the hydroxylation step 110 may be maintained at the desired pH level by controlling the quantity of hydroxide precipitant 104 that is added to the reactor 112 during the hydroxylation step 110, e.g., during the precipitation of thorium from the acidic solution 102.

It has also been found that the desirable range of pH values for the selective precipitation of thorium is dependent upon the concentration of solubilized thorium in the acidic solution 102. In particular, it has been found that increased pH values within the range of about pH 3.5 to pH 4 may be utilized to selectively precipitate thorium as a thorium hydroxide product 108 without precipitating significant amounts of REEs when the concentration of thorium in the acidic solution 102 is relatively low. That is, as the concentration of the thorium in the acidic solution 102 decreases, the pH during the hydroxylation step 110 may be increased to remove additional thorium without removing undesirable quantities of REEs. In one example, the acidic solution 102 can be diluted (e.g., with water) to reduce the thorium concentration, and the hydroxylation step 110 may carried out at a higher pH (e.g., pH 3.5 to pH 3.9) without precipitating undesirable quantities of REEs. In one characterization, the acidic solution 102 comprises not greater than about 800 mg/l of thorium, such as not greater than 500 mg/l, or even not greater than about 200 mg/l thorium, and the contacting step is carried out at a pH of at least about pH 3.5, such as at least about pH 3.6, at least about pH 3.7, and even at least about pH 3.8, but not greater than pH 4, such a not greater than pH 3.9. However, it is believed that at least about 50 mg/l of thorium is required in the solution for precipitation of thorium to occur.

The acidic solution 102 and the hydroxide precipitant 104 should remain in contact (e.g., in reactor 112) for a period of time sufficient to precipitate a majority (e.g., at least about 50%) of the thorium from the acidic solution 102 and form a thorium depleted solution 106 and a thorium hydroxide product 108. In one characterization, the time of contact (e.g., the average residence time in the reactor) during the hydroxylation step 110 may be at least about 30 minutes and may be not greater than about 90 minutes. It is an advantage of this embodiment that the hydroxylation step 110 may be carried out at ambient temperatures, e.g., the step does not typically require the reactor 112 to be heated or cooled. Further, the hydroxylation step 110 may be carried out at ambient pressures, e.g., the step does not require a sealed or otherwise pressure-controlled reactor 112.

After the contacting step 110, the thorium hydroxide product 108 may be separated from the thorium depleted solution 106 in a separating step 114. For example, a filter 116 may be used to filter the output stream 107 containing thorium hydroxide and the thorium depleted solution 106 from the reactor 112 and retain the thorium hydroxide product 108 on the filter 116. The thorium depleted solution 106 (i.e., the filtrate), containing high levels of REEs and very low levels of thorium, may be further treated as is discussed below. The thorium hydroxide product 108 may advantageously be of high purity, i.e., the product may comprise at least about 99 wt. % thorium hydroxide, such as at least about 99.9 wt. % thorium hydroxide. The thorium hydroxide product 108 may be disposed of, or may be a salable commodity particularly in view the high purity of the thorium hydroxide product 108.

As is noted above, thorium precipitation from the acidic solution may be enhanced with increased pH (e.g., up to about pH 4) and with a decreased concentration of thorium in the acidic solution and with low free acid content. In one example of this embodiment, this finding may be applied in a multi-step (e.g., two-step) process. Specifically, the thorium extraction method of this embodiment may include a first hydroxylation step that includes contacting an acidic solution with a hydroxide precipitant at a first pH, e.g., of at least about pH 3 and not greater than about pH 4, to precipitate a thorium hydroxide product containing very low amounts of REEs and form an intermediate thorium depleted solution, i.e., having a lower concentration of thorium than the acidic solution. The intermediate thorium depleted solution may then be subjected to a second hydroxylation step where the intermediate thorium depleted solution is contacted with a hydroxide precipitant at a second pH of at least about pH 3.1 and not greater than about pH 4.2, where the second pH is greater than the first pH to remove additional thorium. In one particular characterization of this method, the pH during the first hydroxylation step is from about pH 3.0 to about pH 3.3, and the pH during a second hydroxylation step is from about pH 3.5 to about pH 4. In this regard, the pH in the second hydroxylation step may be carried out at such higher pH to aggressively remove thorium, even in the event some REEs may precipitate with the thorium hydroxide product, as is discussed below.

In this embodiment, some additional solubilized thorium is precipitated as thorium hydroxide in the second hydroxylation step to form a thorium depleted solution, i.e., having a lower concentration of thorium than the intermediate thorium depleted solution, and that also has a relatively high concentration of REEs in solution. As compared to the embodiment described with respect to FIG. 1, the thorium depleted solution from the second hydroxylation step may be recycled to the first hydroxylation step so that only small concentrations of REEs report with the thorium hydroxide product.

Figure 2:
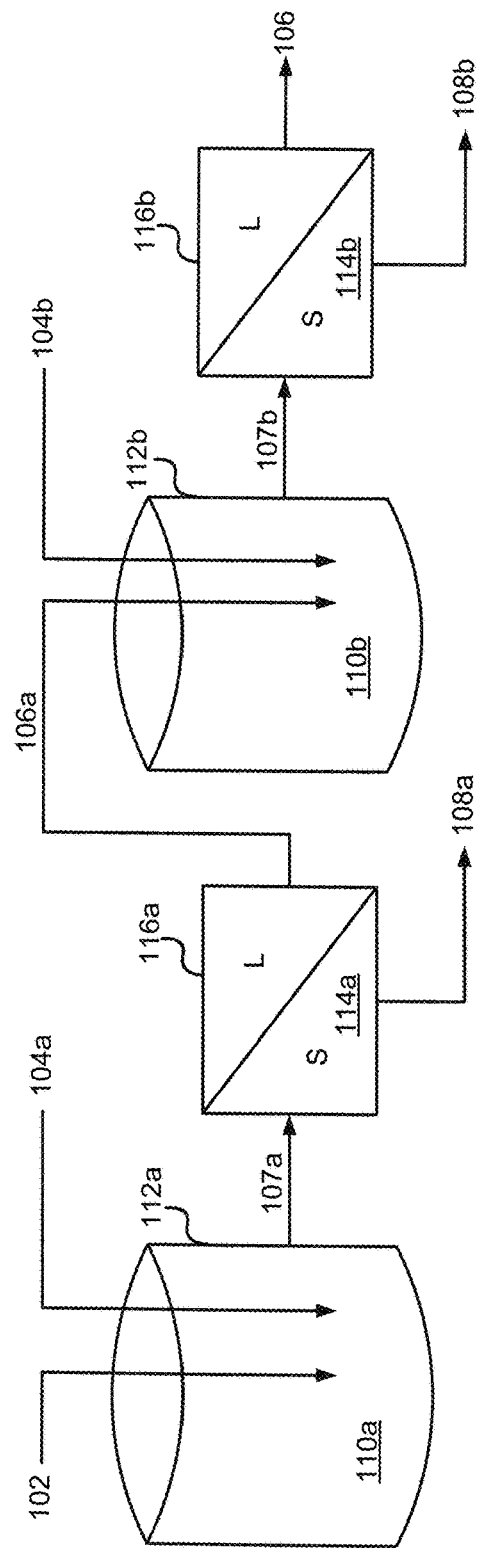
FIG. 2 is a schematic flowsheet illustrating a method for the selective precipitation of thorium as thorium hydroxide from an acidic solution using multiple hydroxylation steps.

Referring now to FIG. 2, this exemplary method may include a first hydroxylation step 110a where the acidic solution 102 is contacted with a first hydroxide precipitant 104a, such as in a first reactor 112a, under conditions such that at least a portion of the thorium in the acidic solution 102 precipitates as a first thorium hydroxide product 108a and a substantial majority of the REEs (e.g., at least about 99 at. % of the REEs) remain solubilized in an intermediate thorium depleted acidic solution 106a. For example, at least about 50 at. % of the thorium in the acidic solution 102 may be precipitated in reactor 112a and removed in a first separation step 114a, e.g., using a filter 116a. In one particular characterization, at least about 60 at. % and not greater than about 90 at. % of the thorium in the acidic solution 102 is separated from the intermediate thorium depleted solution 106a in the separation step 114a as a thorium hydroxide product 108a. As a result, the intermediate thorium depleted solution 106a recovered from the separation step 114a has a lower concentration of thorium than the acidic solution 102.

As is discussed above, the lower concentration of thorium in the intermediate thorium depleted solution 106a advantageously enables a higher pH to be utilized in a second hydroxylation step 110b (i.e., as compared to the first hydroxylation step 110a), e.g., in a second reactor 112b. Thus, in a second separation step 114b, a second thorium hydroxide product 108b is separated from the thorium depleted solution 106. The thorium depleted solution 106 from the separation step 114b may advantageously include not greater than about 5% of thorium contained in the acidic solution 102, such as not greater than about 2% of the thorium contained in the acidic solution 102. Further, due to the high selectivity of the process, at least about 95%, such as at least about 98%, of REEs in the acidic solution 102 may remain solubilized in the thorium depleted solution 106. Although illustrated as a two-step process in FIG. 2 (e.g., including two hydroxylation steps), the method may include additional incremental steps if desired for enhanced thorium precipitation and/or enhanced REE recovery.

Further, the amount of thorium hydroxide product 108b that is separated from the thorium depleted solution 106 may be relatively small, as compared to the amount of thorium hydroxide product 108a that is separated from the intermediate thorium depleted solution 106a. Further, the thorium hydroxide product 108b may include some REEs (due to the higher pH used in hydroxylation step 110b). In one characterization, the thorium hydroxide product 108b may include up to about 20 at. % REEs on a metals basis. Therefore, in one example, the thorium hydroxide product 108b may be recycled back to the first hydroxylation step 110a, so that the recovery of REEs in the thorium depleted solution 106 is increased. That is, any increase in the amount of REEs precipitated as REE-hydroxides in hydroxylation step 110b may be mitigated by recycling the thorium hydroxide product 108b to hydroxylation step 110a, keeping the REEs in the circuit. Thus, in this example, all of the thorium hydroxide may be extracted from the circuit with the thorium hydroxide product 108a.

In one example of the foregoing embodiments, ammonium hydroxide is utilized as a hydroxide precipitant 104/104a/104b to precipitate thorium as thorium hydroxide. For example, ammonium hydroxide may be added as an aqueous solution having a concentration of from about 10% to about 20% ammonium hydroxide, e.g., about 15%. As a result, the thorium depleted solution 106 recovered from the separation step(s) 114 will contain substantial amounts of ammonium nitrate ($NH_4NO_3$), dissolved in the thorium depleted solution 106. As is discussed in more detail below, it may be desirable to continuously or intermittently extract the ammonium nitrate, which is a valuable and salable by-product.

In some embodiments of the present disclosure, methods for the formation of the acidic solution are provided. Further, methods for the extraction of REEs from the thorium depleted solution are provided. In some examples, it may be advantageous to integrate the method(s) described above for the precipitation of thorium from an acidic solution with a solvent extraction circuit for extracting REEs from the thorium depleted solution. It may also be advantageous to integrate a method for the formation of the acidic solution, before hydroxylation, by acid digestion of rare earth compounds, particularly acid digestion of REE-carbonates. In one particular embodiment, reagent consumption may be reduced and overall operating expenses of the process reduced by recycling nitric acid from a solvent extraction circuit to an acid digestion step to form the above-described acidic solution. In one characterization, nitric acid consumption may be reduced to almost zero, with only make-up nitric acid being added to the process to compensate for normal evaporation and leakage losses.

Figure 3:
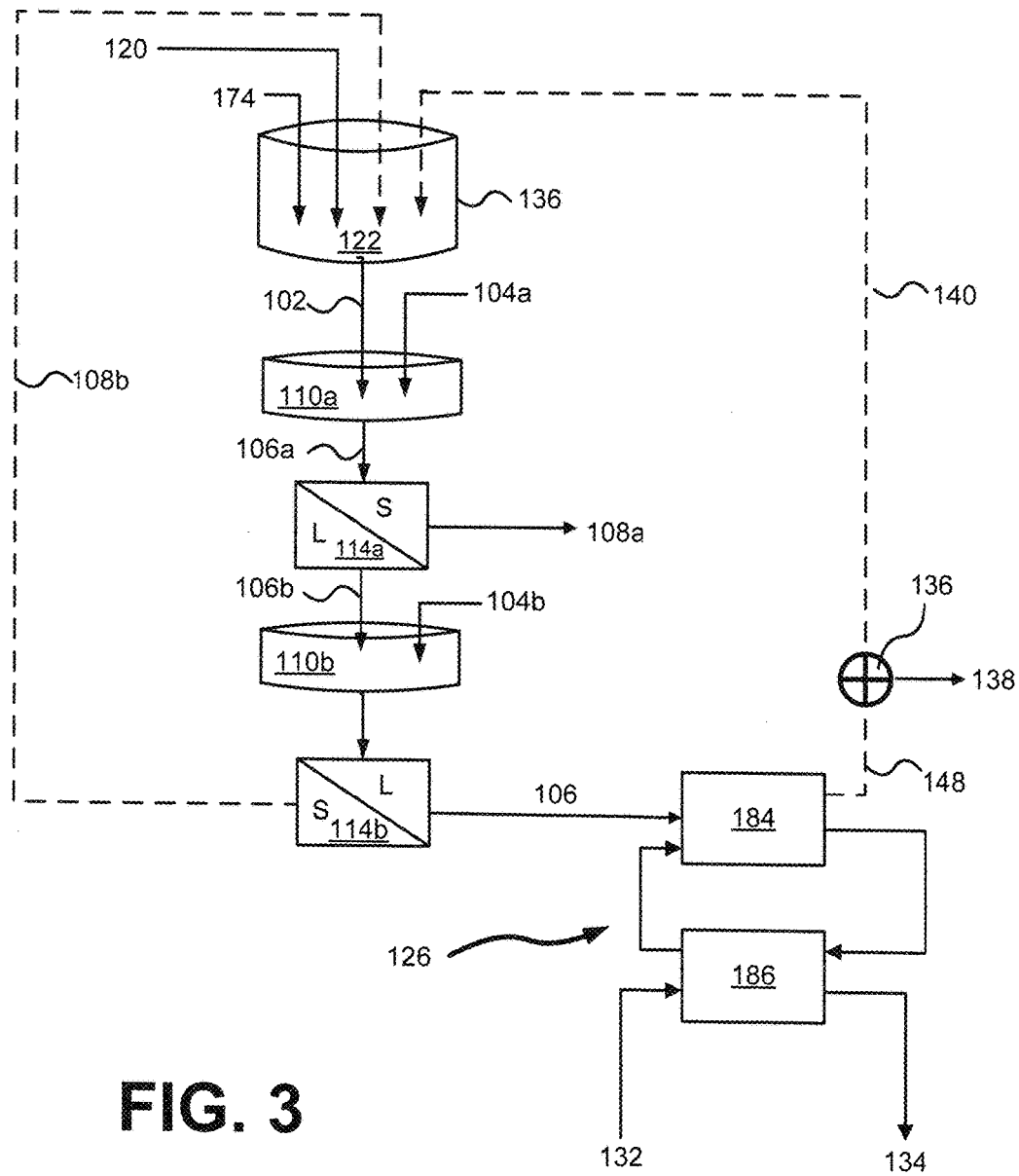
FIG. 3 is a schematic flowsheet illustrating a method for the precipitation of thorium as thorium hydroxide from an acidic solution including the recycle of acid from a solvent extraction circuit.

In one example, the acidic solution is formed by the acid digestion of an REE-carbonate product, such as one that has a high purity with respect to REEs. As illustrated in FIG. 3, an REE-carbonate product 174 may be contacted with an acid 120 (e.g., fresh nitric acid or sulfuric acid) in an acid digestion step 122, such as in a reactor 124. The resulting acidic solution 102 may be an acidic solution substantially as described above with respect to FIGS. 1 and 2. The acidic solution 102 may be contacted in a first hydroxylation step 110a with a hydroxide precipitant 104a to precipitate a thorium hydroxide product 108a from the acidic solution 102. The thorium hydroxide product 108a may be separated from the thorium depleted solution 106b in a separation step 114a. Thereafter, as illustrated with respect to FIG. 2, the intermediate thorium depleted solution 106b may be contacted in a second hydroxylation step 110b with a second hydroxide precipitant 104b to form the thorium depleted solution 106. The thorium depleted solution 106 may then separated from the second thorium hydroxide product 108b in a separation step 114b.

As is noted above, the amount of thorium hydroxide product 108b may be relatively small and there may be appreciable quantities of REEs in the thorium hydroxide product 108b. To reduce losses of REEs, the thorium hydroxide product 108b may be recycled back to the process, and as illustrated in FIG. 3, the second thorium hydroxide product 108b is recycled back to the acid digestion step 122 where the thorium is re-digested with the REE-carbonate product 174. In this manner, all of the thorium hydroxide is removed from the acidic solution 102 with the first thorium hydroxide product 108a. When the thorium hydroxide product 108b is separated in separating step 114b, the resulting thorium depleted solution 106 is a relatively high purity RE-nitrate solution.

The high purity RE-nitrate solution 106 may then be subjected to a solvent extraction circuit 126 to extract REEs from the thorium depleted solution 106. It is an advantage of this embodiment that having the REEs solubilized in nitrate media may reduce the expenses associated with a solvent extraction circuit. The solvent extraction circuit 126 may include the steps of solvent extraction 128 and solvent stripping 130 with a stripping solvent 132. Solvent extraction circuits for the recovery of REEs are known in the art and will not be described here in additional detail. However, because the thorium depleted solution 106 described herein is of extremely high purity, the solvent extraction circuit 126 may advantageously be operated at a reduced capital expense and reduced operating expense. The resulting products are very high purity and high value REEs 134.

As is noted above, the thorium depleted solution 106 may include substantial quantities of highly salable ammonium nitrate. Thus, an ammonium nitrate removal step 136 may be utilized to continuously or intermittently remove ammonium nitrate 138 from the solution 106. As illustrated in FIG. 3, the ammonium nitrate is removed after the solvent extraction circuit 126, as the presence of ammonium nitrate in the thorium depleted solution 106 is not believed to impair the efficacy of the solvent extraction circuit 126. However, it will be appreciated that the ammonium nitrate separation step may also occur before the solvent extraction circuit 126 if desired.

The ammonium nitrate separation step 136 may include cooling the thorium depleted solution to a reduced temperature (e.g., below about 10° C.) to crystallize ammonium nitrate 138. Because ammonium nitrate 138 is highly soluble in acid, it may only be necessary to intermittently operate the separation step 136 to remove ammonium nitrate 138. Ammonium nitrate is valuable and salable by-product that is widely used in the fertilizer industry and may represent a significant source of revenue from the process.

As illustrated in FIG. 3, after separation of the ammonium nitrate 138 (intermittently or continuously), the nitric acid 140 (e.g., recycled nitric acid) may be recycled back to the process, e.g., back to the acid digestion step 122. Thus, the acid (e.g., input at 120) may be contained in an essentially "closed loop" within the process. Additional nitric acid may be generated during the solvent extraction circuit due to cationic ion exchange releasing protons into solution. In this regard, a substantial quantity of the nitric acid required for the acid digestion step may be provided by the recycled nitric acid 140, and only a small amount of fresh nitric acid 120 may be required for the process once steady state and continuous operations are achieved and maintained.

FIG. 3 illustrates the integration of a solvent extraction circuit for the extraction of high purity REEs as metals from the nitrate solution containing the REEs. In other embodiments, it may be advantageous to integrate the method(s) described herein for the precipitation of thorium from an acidic solution with a circuit for precipitating the REEs, e.g., as REE-oxides and/or REE-hydroxides.

Figure 4:
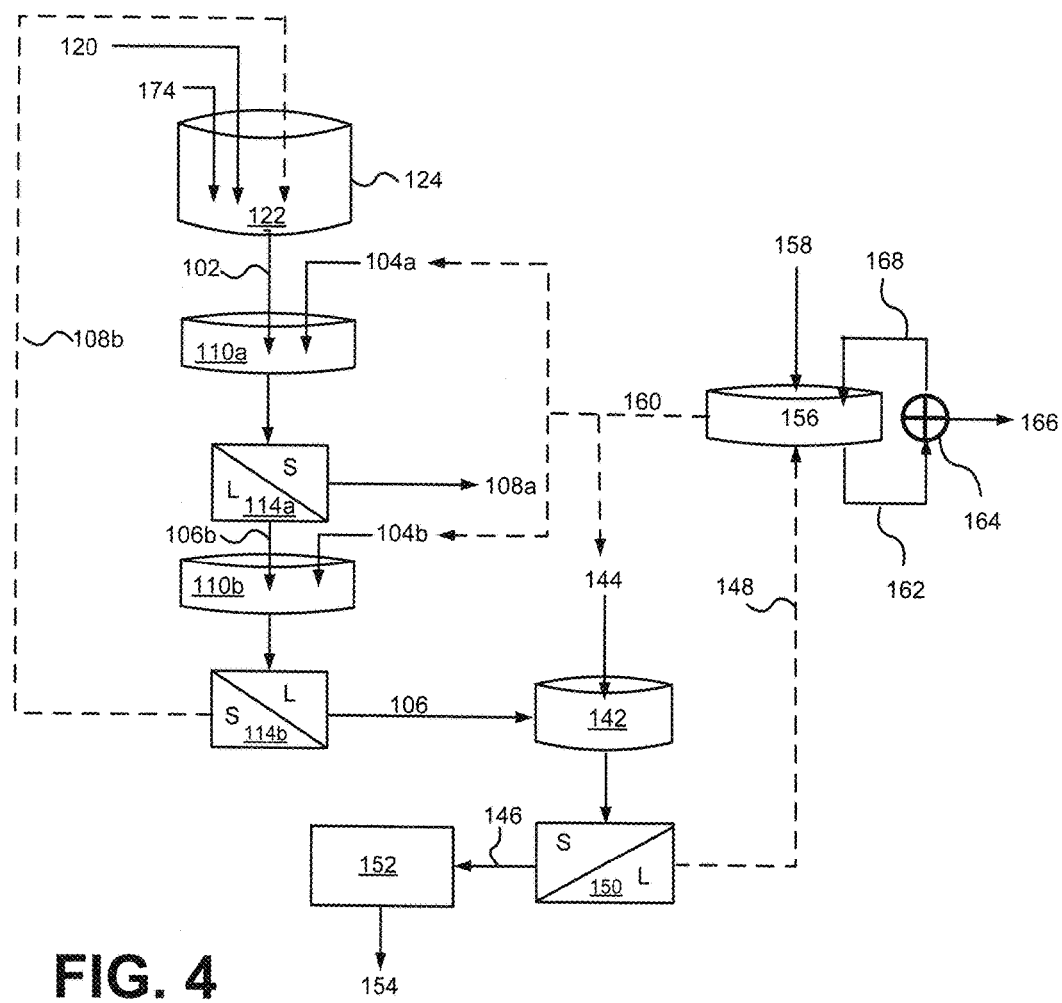
FIG. 4 is a schematic flowsheet illustrating a method for the precipitation of thorium as thorium hydroxide from an acidic solution including the precipitation of rare earth element hydroxides from a nitric acid solution.

In this regard, FIG. 4 illustrates an example of an integrated process similar to the process illustrated in FIG. 3, but where an REE precipitation circuit replaces the solvent extraction circuit of FIG. 3. Thus, the thorium depleted and REE-nitrate rich solution can be treated to precipitate high purity REE-compounds such as REE-oxides and/or REE-hydroxides which, for example, may be shipped to a separate facility for extraction of the REEs as metals.

Referring to FIG. 4, the thorium depleted solution 106 from the separation step 114b will typically have a pH in the range of about pH 3.6 to about pH 4 (e.g., about pH 3.8) and will be rich in REE-nitrates and may contain no, or extremely low levels of, thorium and/or uranium. For example, the solution 106 may include not greater than about 1 ppm thorium and/or uranium. As illustrated in FIG. 4, this solution 106 is conveyed to an REE precipitation step 142, where the solution 106 is contacted with an REE precipitation agent 144. In one characterization, ammonium hydroxide is used for precipitation in both the precipitation step 144 to precipitate REEs and in the hydroxylation step(s) 110a/110b to precipitate thorium. The REE precipitation agent 144 may be added to the solution 106 in sufficient quantities to increase the pH of the solution, such as by increasing the pH to at least about pH 4.5, such at least about ph 4.9. In one characterization, the pH during the precipitation step 144 is not greater than about pH 6 and may be about pH 5.5. At these pH levels, the REEs will precipitate from the solution 106 as REE-hydroxides 146, which may be separated from an REE-depleted nitrate solution 148 in a separation step 150.

The REE-hydroxides 146 may then be converted from the REE-hydroxides to REE-oxides. As illustrated in FIG. 4, the REE-hydroxides 146 are conveyed to a drying step 152 where the REE-hydroxides are heated to a drying temperature that is sufficient to convert a substantial majority of the REE-hydroxides 146 to REE-oxides 154. For example, the drying step 152 may include heating the REE-hydroxides 146 to a temperature of at least about 100° C., such as at least about 120° C., and not greater than about 160° C., such as not greater than about 150° C. In one example, the REE-hydroxides 146 are conveyed to a screw feed dryer for the substantially continuous production of the REE-oxides 154. In another example, the REE-hydroxides 146 may be stockpiled as necessary and dried batchwise.

It is an advantage of this embodiment that the resulting REE-oxide product 154 will have a very high purity, particularly with respect to base metals and radioactive metals such as uranium and thorium. In one example, the REE-oxide product 154 has a purity of at least about 99.8%, i.e., the REE-oxide product 154 comprises at least about 99.8% REE-oxides, such as a purity of at least about 99.9%. For example, the REE-oxide product 154 may comprise not greater than about 1 ppm thorium. The uranium content may be not greater than 0.1 ppm, for example, such a not greater than about 0.01 ppm.

An REE-depleted nitrate solution 148 may also recovered from the separation step 158, and may have a high content of ammonium nitrate, such as from about 30 g/l to about 50 g/l ammonium nitrate. The solution 148 may be recycled to preserve nitrates and in particular to preserve ammonium in the process. As illustrated in FIG. 4, the REE-depleted nitrate solution 148 may be conveyed to a vessel 156 where ammonium hydroxide is stored for use in the process, i.e., where the recycled nitrate solution 148 is added to fresh ammonium hydroxide 158. An ammonium hydroxide product 160 such as an ammonium hydroxide solution may then be conveyed as needed to the process, e.g., to hydroxylation steps 110a/110b and/or to REE precipitation step 142. Because the recycled REE-depleted nitrate solution will contain ammonium nitrates, it may be desirable to remove the ammonium nitrates from the ammonium hydroxide vessel 156 on a continuous or intermittent basis. In this regard, a portion 162 of the solution contained within vessel 156 may be periodically bled off from the vessel 156 and subjected to an ammonium nitrate precipitation step 164 to crystallize an ammonium nitrate by-product 166 and recycle an ammonium nitrate depleted solution 168 back to the vessel 156. The ammonium nitrate by-product 166 will be of high purity and a valuable by-product of the process.

While one example for the precipitation of REE compounds from the thorium depleted solution have been described in detail, it will appreciated that other methods may be applied. For example, in some examples, it may be desirable to directly precipitate the REEs as REE-nitrates from the thorium depleted solution.

As is noted above, the acidic solution 102 may contain REEs in addition to thorium, and may be formed by the dissolution of a variety of compounds in an acid (e.g., dissolution by acid digestion). In some of the embodiments disclosed herein, it is desirable that the REEs are in the form of REE-oxalates, e.g., $RE_2(C_2O_4)_3$ or $RE_3(C_2O_4)_3$, where RE is a rare earth element. However, the solubility of REE-oxalates in acid is very low. Thus, in one example, the acidic solution 102 is formed by the dissolution of carbonate compounds, such as $RE_2(CO)_3 \cdot xH_2O$ where RE is a rare earth element, and $Th(CO_3)_2 \cdot xH_2O$, as illustrated above in FIG. 3. The REE-carbonates may be formed by a variety of methods, and in one example the REE-carbonates are formed from REE-oxalates by a metathesis reaction to render the REEs soluble in an acid such as nitric acid.

Figure 5:
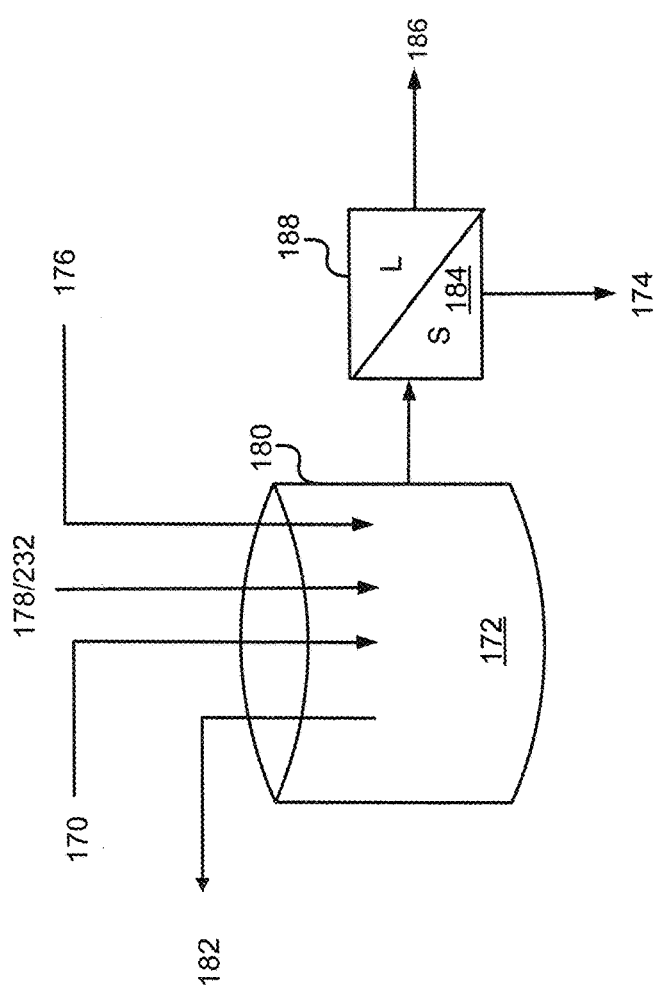
FIG. 5 is a schematic flowsheet illustrating a method for the conversion of a rare earth oxalate product to a rare earth carbonate product by metathesis.

In the embodiment illustrated in FIG. 5, an REE-oxalate product 170 is converted in a metathesis step 172 to a REE-carbonate product 174 for subsequent dissolution of the REE-carbonate product 174 in an acid, e.g., to solubilize the REEs and thorium in an acidic solution 102 (FIG. 3). In this embodiment, an REE-oxalate product 170 is contacted with a carbonate compound 176 such as sodium carbonate ($Na_2CO_3$) in the metathesis step 172, along with a solvent 178 such as water, which may be introduced with the other reactants or introduced separately. For example, the metathesis step 172 may include contacting the reactants in a reactor 180 for a period of time sufficient to convert at least about 98%, such as at least about 98.5% of the REEs in the REE-oxalate product 170 to REE-carbonates in the REE-carbonate product 174. Similarly, the metathesis step 172 may be carried out for a period of time sufficient to convert at least about 98%, such as at least about 98.5% of thorium in the REE-oxalate product 170 from thorium oxalate to thorium carbonate in the REE-carbonate product 174. The only by-product of the metathesis step 172 is a high-purity carbon dioxide stream 182 which may be captured as a by-product.

In a separation step 184, the REE-carbonate product 174 (e.g., REE-carbonate particulates) may be separated from an oxalate solution 186 such as by using a filter 188. The oxalate solution 186 will include substantial amounts of dissolved oxalates (e.g., $Na_2C_2O_4 \cdot yH_2O$ when the carbonate compound 176 is sodium carbonate) and in some examples discussed below, the oxalate solution 186 may advantageously be recycled to a step where REEs are precipitated as the REE-oxalate product 170.

Another embodiment of the present disclosure is directed to the integration of several of the above-described methods in a process for extracting REEs from an REE-oxalate product by applying a metathesis reaction to convert the REE-oxalates to REE-carbonates, digesting the REE-carbonates in an acid to form an REE-rich solution, and selectively precipitating thorium from the REE-rich solution. The resulting high purity REE-nitrate solution may then be treated in a solvent extraction circuit to extract the REEs, or may be processed to recover a dry powder of REE-nitrates, REE-oxides or REE-hydroxides.

Figure 6:
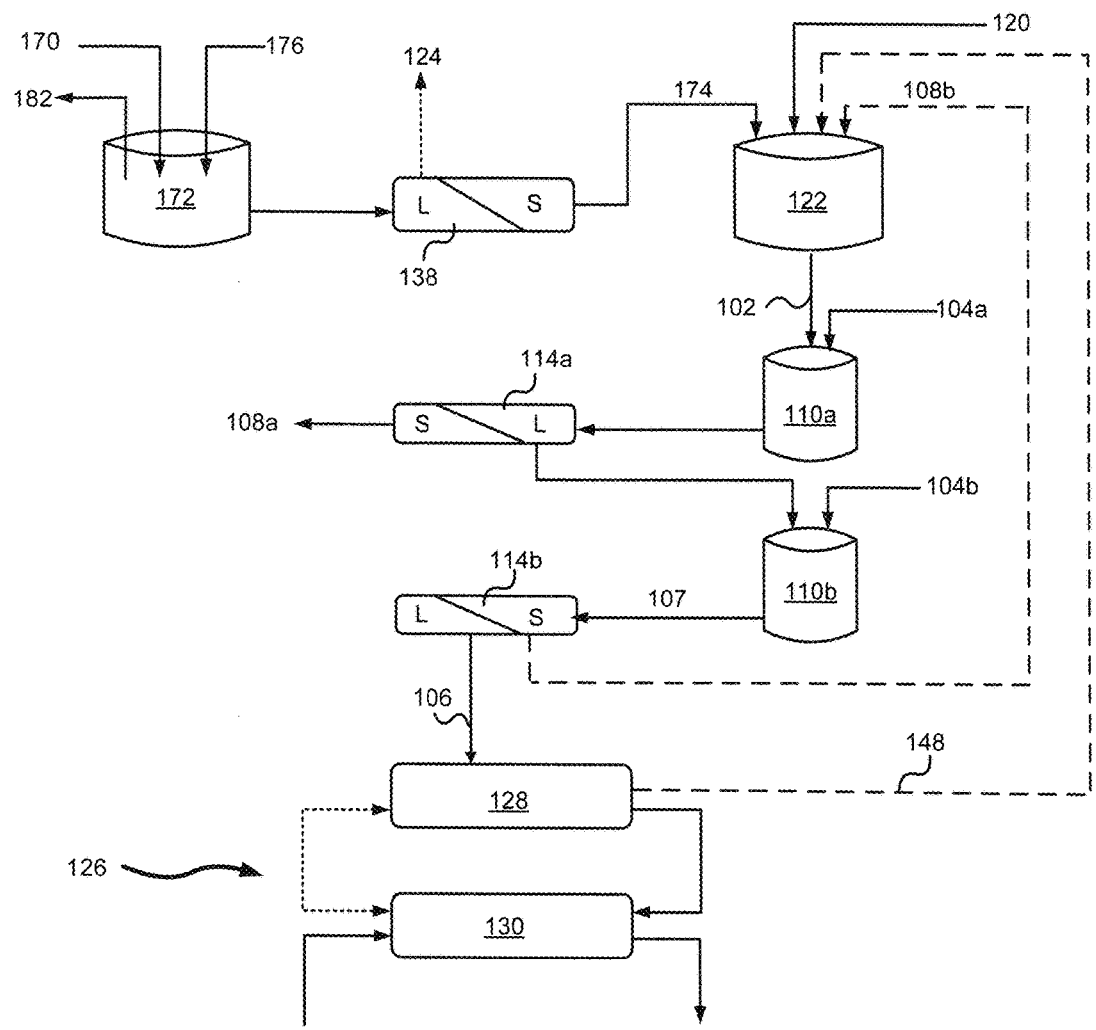
FIG. 6 is a schematic flowsheet illustrating a method for the conversion of a rare earth oxalate product to a rare earth carbonate product by metathesis including the recycle of acid from a solvent extraction circuit.

As illustrated in FIG. 6, a metathesis step 172 may be carried out by contacting an REE-oxalate product 170 and a carbonate compound 176 such as sodium carbonate in a reactor to form an REE-carbonate product 174 and an oxalate solution 186, e.g., an oxalate solution containing dissolved sodium carbonate. The REE-carbonate product 174 is then subjected to an acid digestion step 122 where the REE-carbonate product 174 may be contacted with nitric acid, e.g., fresh nitric acid 120 and/or recycled nitric acid 140 such as from a subsequent solvent extraction circuit 126. Recycled thorium hydroxide product 108b from a downstream hydroxylation step 110b may also be added to the acid digestion step 122.

The resulting acidic solution 102 containing dissolved carbonates may then be subjected to hydroxylation in steps 110a and 110b to form a thorium hydroxide product 108a which is a high purity thorium hydroxide product containing very small concentrations of REEs. The thorium depleted solution 106 my then be separated from the thorium hydroxide product 108b and subjected to a solvent extraction circuit 126 to extract REEs therefrom, as is described with respect to FIG. 4. The REE-depleted nitrate solution 148 may be recycled, e.g., also as described with respect to FIG. 4.

In another embodiment of this disclosure, a method for the formation of REE-oxalates from a solution, such as a pregnant liquor solution ("PLS") is provided. The method may include the extraction of the REEs from a PLS in the form of a precipitation product that includes REE-oxalate particulates. In accordance with this embodiment, the precipitation of oxalate compounds (e.g., REE-oxalates) from a PLS containing REEs and other elements (e.g., base metals, uranium and other metals) advantageously may result in a very high purity REE-oxalate product having a very low concentration of non-REE elements. Further, certain embodiments provide for the recycling of oxalic acid and/or oxalate compounds to reduce the overall consumption of oxalic acid by the process.

Figure 7:
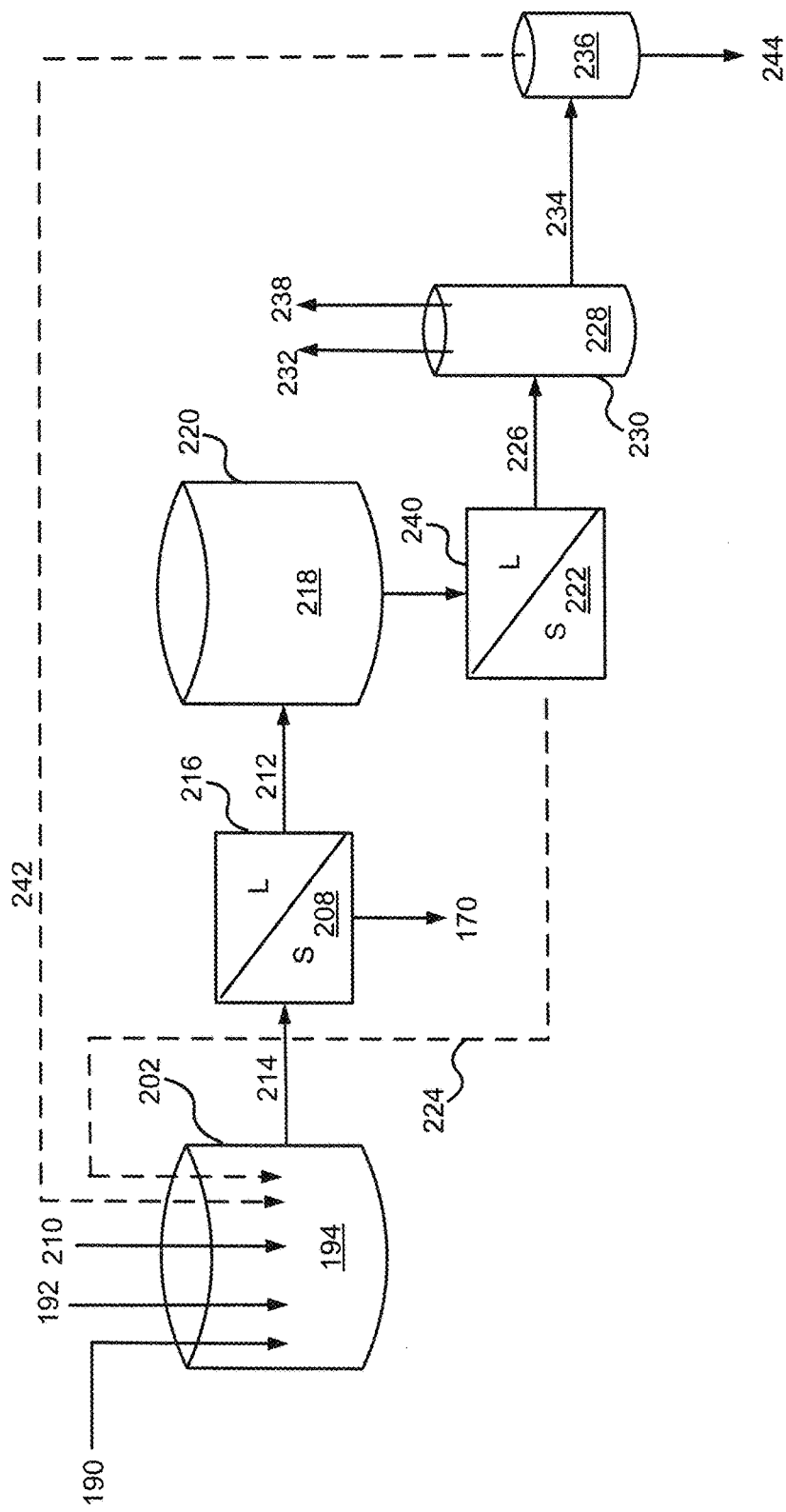
FIG. 7 is a schematic flowsheet illustrating a method for the precipitation of rare earth elements as rare earth oxalates from a pregnant liquor solution.

FIG. 7 schematically illustrates one such method for the formation of an REE-oxalate product having low concentrations of non-REE elements. As illustrated in FIG. 7, a PLS 190 is contacted with oxalic acid ($H_2C_2O_4$) 192 in an oxalate formation step 194. The PLS 190 may include one or more REEs, i.e., REEs that have been dissolved (e.g., solubilized) in the PLS 190. For example, the PLS 190 may be an acidic solution (e.g., from a chloride leach) and the REEs may be present as dissolved salts, such as dissolved chloride salts. In one example, the PLS 190 includes a concentration of REEs of at least about 20 g/l. For example, the PLS 190 may include at least about 25 g/l REEs, such as at least about 30 g/l REEs, at least about 35 g/l REEs, or even at least about 40 g/l REEs.

The PLS 190 may also include non-REE elements that are solubilized in the PLS 190. The non-REE elements may include metallic elements, particularly: alkali metals such as sodium (Na) and potassium (K); alkaline earth metals such as magnesium (Mg), calcium (Ca), strontium (Sr) and barium (Ba); transition metals such as nickel (Ni), copper (Cu), zirconium (Zr), iron (Fe), manganese (Mn) and titanium (Ti); post-transition metals such as lead (Pb) and aluminum (Al); metalloids such as silicon (Si); and radioactive metals (e.g., actinides) such as thorium (Th) and uranium (U). The non-REE elements may also include non-metallic elements such as sulfur (S) and phosphorous (P). Among the foregoing, and in certain characterizations, the PLS 190 may particularly include Mn in concentrations of at least about 10 g/l and/or may include Fe in concentrations of at least about 20 g/l.

It is a particular advantage of the oxalate formation step 194 of this embodiment that a substantial majority of the non-REE elements do not report with the REE-oxalate product 170, i.e., they remain solubilized in an REE-depleted solution 198.

Exemplary compositions of pregnant liquor solutions are illustrated in Table I.

TABLE I

| Element | PLS Example 1 (mg/l) | PLS Example 2 (mg/l) | PLS Exemplary Range (mg/l) |
|---------|----------------------|----------------------|-----------------------------|
| F       | 3610                 | 3380                 | 3000-4000                   |
| Al      | 4555                 | 4593                 | 4000-5000                   |

TABLE I-continued

| Element | PLS Example 1 (mg/l) | PLS Example 2 (mg/l) | PLS Exemplary Range (mg/l) |
|---|---|---|---|
| Ba | 2126 | 2147 | 2000-2500 |
| Ca | 3045 | 3151 | 3000-3200 |
| Fe | 22838 | 22733 | 22000-30000 |
| K | 1638 | 1653 | 1000-2000 |
| Mg | 1892 | 1995 | 1000-2000 |
| Mn | 13349 | 13514 | 10000-14000 |
| Na | 17733 | — | 10000-180000 |
| P | 70 | 71 | 60-80 |
| Pb | 1011 | 1058 | 1000-1200 |
| S | <100 | <100 | 10-80 |
| Si | 47 | 49 | 40-50 |
| Th | 40 | 70 | 40-70 |
| Ti | 296 | 309 | 250-350 |
| U | 40 | 34 | 30-60 |
| Zn | 1210 | 1297 | 1000-3000 |
| REEs | 35737 | 36369 | >35000 |

As can be seen from Table I, pregnant liquor solutions, e.g., from the leaching of a rare earth ore concentrate with HCl, may also contain appreciable amounts of non-REE elements, including base metals and other undesirable metals such as uranium and thorium. It is a significant advantage of this embodiment that REE-oxalates may be precipitated from the PLS, while a substantial majority of the non-REE elements remain in solution, i.e., do not form oxalate compounds during the oxalate formation step. Particularly, very low concentrations of elements such as Al, Fe, Ca, Mg, n. P, Pb, S, Ti, U and/or Zn will precipitate with the REE-oxalates. As a result, the REE-oxalate product is of very high purity and a substantial proportion of the base metals and other metals such as uranium can be removed prior to extraction of the REEs, e.g., in a solvent extraction process.

The oxalate formation method of this embodiment to extract REEs includes contacting the PLS 190 with oxalic acid 192 in an oxalate formation step 194, such as by contacting the reactants in a reactor 194 (e.g., a sealed reactor) under conditions such that REE-oxalate compounds (e.g., $RE_2(C_2O_4)_3$, $RE_3(C_2O_4)_3$, where RE=rare earth) precipitate from the PLS 190. It will be appreciated that the REE-oxalate compounds may also be hydrated, e.g., $RE_2(C_2O_4)_3 \cdot xH_2O$. The PLS 190 is an acidic solution and may, for example, include free chloride ions. For example, the PLS 190 may comprise hydrochloric acid (HCl) and may be obtained from the leaching of rare earth minerals (e.g., a rare earth ore concentrate) with HCl. In one example, the PLS 190 has a free acid concentration (HCl) in the range of from about 0.5M to about 1M (e.g., about 18.2 g/l to about 35.5 g/l HCl).

A sufficient amount of oxalic acid 192 is contacted with the PLS 190 in the reactor 202 to precipitate a majority of the REEs as REE-oxalates in an REE-oxalate product 170. For example, the oxalic acid 192 (e.g., fresh oxalic acid) input to reactor 202 may be an aqueous solution having a concentration of fresh oxalic acid in the range of at least about 38.4 g/l to about 52.5 g/l. Excess oxalic acid may be required and may be obtained by recycling various product streams in the process as is described herein.

Sodium oxalate ($Na_2C_2O_4$) 210 may also be contacted with the PLS 190 in the oxalate formation step 194, such as by adding the sodium oxalate 210 to the oxalic acid 192, or by adding the sodium oxalate 210 directly to the PLS 190 in reactor 194. As is illustrated in FIG. 7, the sodium oxalate 210 may advantageously be recycled from a subsequent process step, such as from crystallization step 206, describe below. Alternatively, or in addition to, fresh sodium oxalate may be added to the oxalate formation step 194. In one example, the ratio of (fresh) oxalic acid 192 to sodium oxalate 210 may be greater than 1, and in one particular characterization, the ratio of oxalic acid 192 to sodium oxalate 210 may be at least about 3:1 and not greater than about 4:1, such about 3.5:1. The addition of recycled sodium oxalate 210 to the oxalate formation step 194 may advantageously reduce the total consumption of oxalic acid by the process. This reduction in oxalic acid consumption may represent a significant cost savings for the process.

The oxalate formation step 194 may be carried out under reaction conditions such that the formation of REE-oxalates is favored over the formation of most non-REE oxalates from the PLS 190. In one characterization, the oxalate formation step 194 is carried out by maintaining the reactants (e.g., PLS 190, oxalic acid 192 and optionally sodium oxalate 210) at an elevated precipitation temperature (e.g., a controlled precipitation temperature above ambient) of at least about 50° C. and not greater than about 90° C., such as at least about 60° C. or at least about 70° C., and not greater than about 85° C. It has been found that a very high proportion of the REEs dissolved in the PLS 190 will precipitate as REE-oxalate particulates at such precipitation temperatures, while a comparatively low quantity of most non-REE elements (e.g., with the exception of thorium) will precipitate from the PLS 190. Precipitation temperatures at the higher end of this range (e.g., from about 75° C. to about 85° C.) may result in higher purity metal oxalates, i.e., a high content of REE-oxalates in the REE-oxalate product 170 and a relatively low content of non-REE oxalates in the REE-oxalate product 170. In one characterization, the oxalate formation step 194 may be carried out by maintaining a precipitation temperature (e.g., in reactor 202) for a sufficient amount of time to precipitate at least about 75 at. % of the REEs in the PLS 190 as particulate REE-oxalates such as, at least about 85 at. % of the REEs., at least about 90 at. % of the REEs, at least about 95 at. % of the REEs, or even at least about 98 at. %, at least about 99 at. % or 99.5 at. % of the REEs. In one example, the oxalate formation step 194 may be carried out for at least about 30 minutes and not greater than about 120 minutes, such as for about 60 minutes. The reactants may also be agitated (e.g., mixed) in the reactor 202 during the oxalate formation step 194.

After formation of oxalate precipitates in the reactor 194, the metal oxalate precipitates may be allowed to crystallize (e.g., to grow) over a period of time and the REE-oxalate product 170 may then be separated from an REE-depleted solution 212 in a separation step 208. For example, the mixture 214 may be allowed to cool over a period of time to allow crystallization of the metal oxalates to form the REE-oxalate product 170.

If the mixture 214 from the oxalate formation step 194 is allowed to cool, it may take a long period of time (e.g., several days) for the metal oxalate precipitates to completely crystallize so that the REE-oxalate product 170 may be readily separated from the REE-depleted solution 212. Alternatively, the temperature of the reactants may be increased to a second crystallization temperature (e.g., greater than the first precipitation temperature) to enhance (e.g., to accelerate) crystallization and growth of the metal oxalate precipitates, particularly of the REE-oxalates. It has been found that because a majority of the initially available oxalate ion ($C_2O_4^{2-}$) is consumed in the formation step 194 at the precipitation temperature, the increase in temperature in the crystallization step will not cause a substantial amount of non-REE elements to precipitate from the PLS 190. The crystallization temperature is greater than the precipitation temperature, and in one characterization, the crystallization temperature is at least about 5° C. greater than the precipitation temperature, such as at least about 7° C. greater than the precipitation temperature. In another characterization, the crystallization temperature is at least about 90° C., such as at least about 92° C. and is not greater than about 100° C., such as not greater than about 98° C. The crystallization of the oxalates may be carried out in the same reactor as the precipitation of the oxalates (e.g., in reactor 194), or may be carried out in a separate reactor (not illustrated).

The crystallization temperature may be maintained for a time sufficient to grow the REE-oxalate particulates to a size that is suitable for subsequent separation 208 from the remaining REE-depleted solution 212. In one characterization, the crystallization temperature is maintained for a period of time sufficient to grow the REE-oxalate precipitates to an average size (e.g., diameter) of at least about 50 nm, such as at least about 65 nm. In one particular characterization, the REE-oxalate precipitates are crystallized to an average size of from about 50 nm to about 85 nm. For example, the crystallization temperature may be maintained for at least about 4 hours and not greater than about 8 hours, such as for about 6 hours.

After crystallization, REE-oxalate product 170 may be separated from the REE-depleted solution 212 in a separation step 208. For example, the separation step 208 may include the use of a micro-filter 216 to separate the REE-oxalate product 170 from the REE-depleted solution 212.

The REE-oxalate product 170 comprises predominately REE-metal oxalates. It is an advantage of the oxalate formation step 194 that the REE-oxalate product 170 may be of high purity. For example, the total non-REE metals (e.g., Ba, Na, K, Si, Sr and/or Th) may constitute not greater than about 5 wt. % of the REE oxalate product 170, such as not greater than about 3 wt. % or even not greater than 1 wt. %. Table II illustrates the elemental metal concentrations of exemplary REE-oxalate products, i.e., expressed as percentages of the total metal content, as determined by inductively coupled plasma (ICP) analysis.

TABLE II

| Element | Ex. 1 Concentration (at. % of total metals) | Ex. 2 Concentration (at. % of total metals) |
|---|---|---|
| REEs | ~98.2 | ~92.5 |
| F | 0.00 | 0.00 |
| Al | <0.01 | <0.01 |
| Ba | 0.44 | 1.00 |
| Ca | 0.16 | <0.10 |
| Fe | 0.16 | 0.58 |
| K | 0.14 | <1.00 |
| Mg | <0.01 | <0.01 |
| Mn | <0.1 | <0.1 |
| Na | 0.08 | <0.1 |
| P | 0.04 | 0.24 |
| Pb | 0.04 | <0.10 |
| S | 0.04 | 0.04 |
| Si | 0.02 | <0.50 |
| Th | 0.52 | 0.58 |
| Ti | 0.02 | <0.10 |
| U | 0.00 | 0.00 |
| Zn | <0.01 | <0.10 |
| Total Non-REEs | ~1.74 | ~7.04 |
| Th + U | ~0.52 | ~0.58 |

As is illustrated by Table II, the oxalate formation step 194 may advantageously selectively precipitate REE-oxalates from the PLS 190, e.g., to the exclusion of non-REE elements such as base metals.

Thus, the REE-depleted solution 212 may be an acidic solution that includes solubilized metals that did not precipitate, e.g., to form a metal oxalate, during the oxalate formation step 194. For example, the REE-depleted solution 212 may include solubilized elements as listed in Table II such as Fe, Mn, Th, U, F, Al, Ca, K, Mg, Na, Sr, Zn, P, S, Pb and Ti. In one characterization, the REE-depleted solution 212 includes not greater than about 0.5 g/l REEs, such as no greater than about 0.25 g/l REEs. In another characterization, the REE-depleted solution 212 contains no greater than about 10 ppm thorium, such as from about 1 ppm to 10 ppm thorium. The REE-depleted solution 212 may have high free acid content, and the free acid content may be higher than the free acid content of the PLS 190. For example, the free acid content (HCl) of the REE-depleted solution 212 may be greater than about 100 g/l, such as greater than about 110 g/l. In another characterization, the free acid content of the REE-depleted solution 212 may be at least about 1.5 times greater than the free acid content of the PLS 190, such as at least about 2 times greater.

As is describe above, the REE-oxalate product 170 may include a high concentration of the REEs in the form of REE-oxalates. In one characterization, at least about 95% of the total metallic elements in the REE-oxalate product 170 are REEs, such as at least about 97% and even at least about 99% of the total metallic elements. Any remaining non-REE metal oxalates (i.e., impurities) may comprise, for example, oxalates of Ba, Na, K, Si and Th. Stated another way, based on the total metals content of the REE-oxalate product 170, the product 170 may include no greater than about 5 at. % non-REE metals, such as no greater than about 3 at. % non-REE metals and even no greater than about 1 at % non-REE metals.

The REE-depleted solution 212 may be recycled to conserve acid (e.g., HCl acid), which may be particularly advantageous due to the relatively high free acid content of the REE-depleted solution 212. For example, as illustrated in FIG. 7, the REE-depleted solution 212 may be transferred to a thickening step 218 such as in a thickener 220. After thickening 218, a separation step 222 may be carried out to separate oxalates 224, which then may be recycled to the oxalate formation step 194, from an acidic solution 226, e.g., an acidic solution that includes a high concentration of chloride ions. The solution 226 may be subjected to a distillation step 228 using a distiller 230 to recover water 232, which may be used as process water in other process steps, and acid 238, which may also be recycled to other process steps such as a leaching step described below. Residue 234 may be further treated in a crystallization step 236 to recover and recycle oxalic acid crystals 242 and a by-product 244 that contains metals. The by-product 244 may be processed to recover further metals of value, such as gold, uranium, aluminum, manganese, iron, magnesium, strontium and zinc. The residue may be transferred to a crystallization step 236, where oxalic acid crystals 176 may be recovered and recycled.

Figure 8:
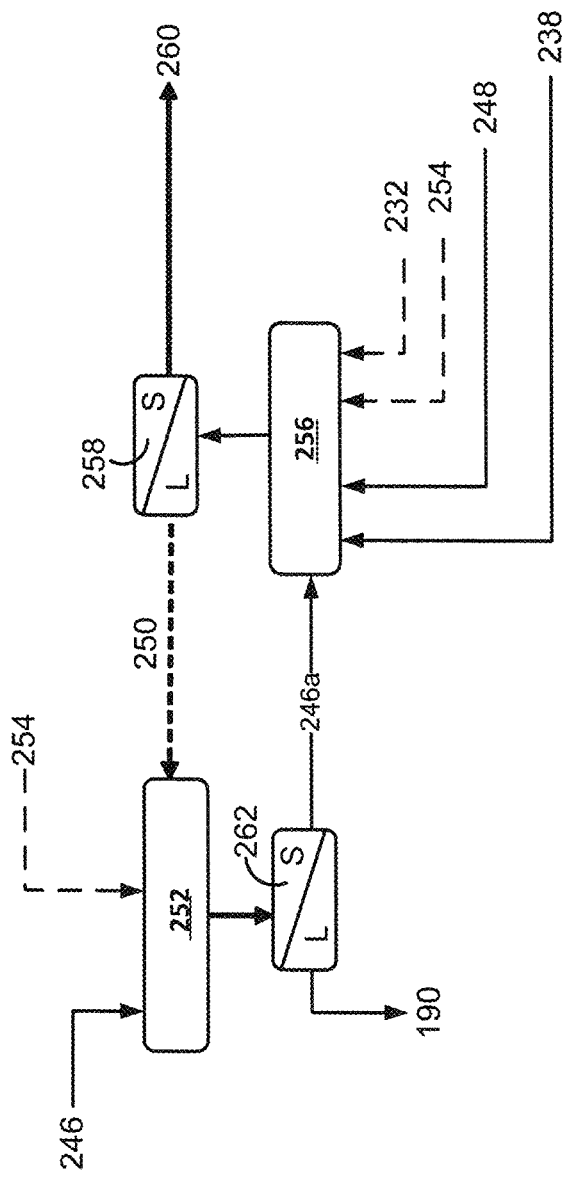
FIG. 8 is a schematic flowsheet illustrating a method for leaching a rare earth ore concentrate to form a pregnant liquor solution.

As is noted above, the PLS 190 may be derived from the leaching of rare earth mineral ore, such as an ore concentrate. FIG. 8 illustrates a schematic flowsheet for one such leaching process. It will be appreciated that the leaching process illustrated in FIG. 8 is only exemplary, and that other leaching processes for forming a pregnant liquor solution may also be employed in accordance with this disclosure.

As illustrated in FIG. 8, the leaching process may include leaching a rare-earth ore concentrate 246 with an acid 248 such as HCl acid in a counter-current flow to enhance leaching efficiency and reduce acid consumption. As is known to those skilled in the art, the ore concentrate 246 may be derived from rare earth containing minerals such as bastnaesite, monazite, carbonatite, loparite, or similar rare earth containing minerals. After separation from waste rock and other debris, the rare earth minerals may be beneficiated (e.g., milled) to reduce particle size and increase surface area of the minerals, and subjected to further separation such as by flotation and/or magnetic separation. A typical rare earth ore concentrate will include about 30% to about 70% rare earth oxides.

To extract metal values from the rare earth ore concentrate 246, the concentrate 246 may be first contacted with recycled PLS 250 (e.g., containing HCl) in a pre-leaching step 252. In addition to the ore concentrate 246 and the recycled PLS 250, the pre-leaching step 252 may optionally include the addition of a reducing compound 254, for example a sulfur-containing compound such as sodium sulfite ($Na_2SO_3$). The addition of a sulfur-containing compound such as sodium sulfite may advantageously precipitate barium (Ba) and radium (Ra) as their sulfates from the PLS 246. Further, the sulfur may reduce iron (Fe) in the PLS 246. Specifically, the compound 254 may be selected to reduce at least a portion of the Fe in the PLS 246 from a +3 oxidation state to a +2 oxidation state. As is described herein, the leaching process may be integrated with a step that includes precipitating REE-oxalates from the PLS 246 by the addition of oxalic acid. However, $Fe^{3+}$ may disadvantageously consume oxalic acid, and may increase the reagent costs for the overall process. By reducing the $Fe^{3+}$ concentration in the PLS 246 and maintaining a substantial majority of the iron in the $Fe^{2+}$ state, downstream consumption of oxalic acid may be reduced.

The pre-leaching step 252 is advantageously integrated (e.g., in counter-current flow) with a primary leaching step 256. In the primary leaching step 256, pre-leached ore concentrate 246a is contacted with additional acid 248 (e.g., HCl) to leach metals from the pre-leached ore concentrate 246a. For example, the primary leaching step 256 may include contacting the pre-leached ore concentrate 246a with fresh HCl 248 and/or recycled HCl 238, e.g., recycled PLS from distillation 228 (FIG. 7). A reducing compound 142 may also be used in the primary leaching step 256, as is described above with respect to pre-leaching step 252. The primary leaching step 256 may be carried out at an elevated temperature, such as at least about 40° C. to not greater than about 95° C., for a period of time and under conditions (e.g., agitation) sufficient to solubilize substantially all of the REEs (e.g., at least about 95 wt. % of the REEs) in the pre-leached ore concentrate 246a. In one particular example, the primary leaching step is carried out of a temperature of from about 50° C. to about 70° C. to reduce dissolution of barium. The use of lower leaching temperatures (e.g., 50° C.) may also reduce the capital expense of the reactor by enabling fiberglass reactors to be utilized. In one characterization, the primary leaching step 256 is carried out for about 6 hours (e.g., for an average residence time of about 6 hours).

After primary leaching 256, a solid/liquid separation step 258 may be carried out to separate an acidic solution 250 comprising REEs from leach solids 260, which then may be treated (e.g., with hydroxides or carbonates) to neutralize the leach solids before disposal as tailings. The acidic solution 250 may be conveyed to the pre-leach step 252, after which the final PLS 190 is separated from the pre-leached ore concentrate 246a in a separation step 262, e.g., in a substantially continuous process.

The RE ore concentrate 246 will typically include other elements in addition to the REEs, including metallic elements and non-metallic elements. Table I above illustrates the predominant elements that may be found in an exemplary pregnant liquor solution (PLS) extracted from the acidic leaching of an RE ore concentrate.

Figure 9A:
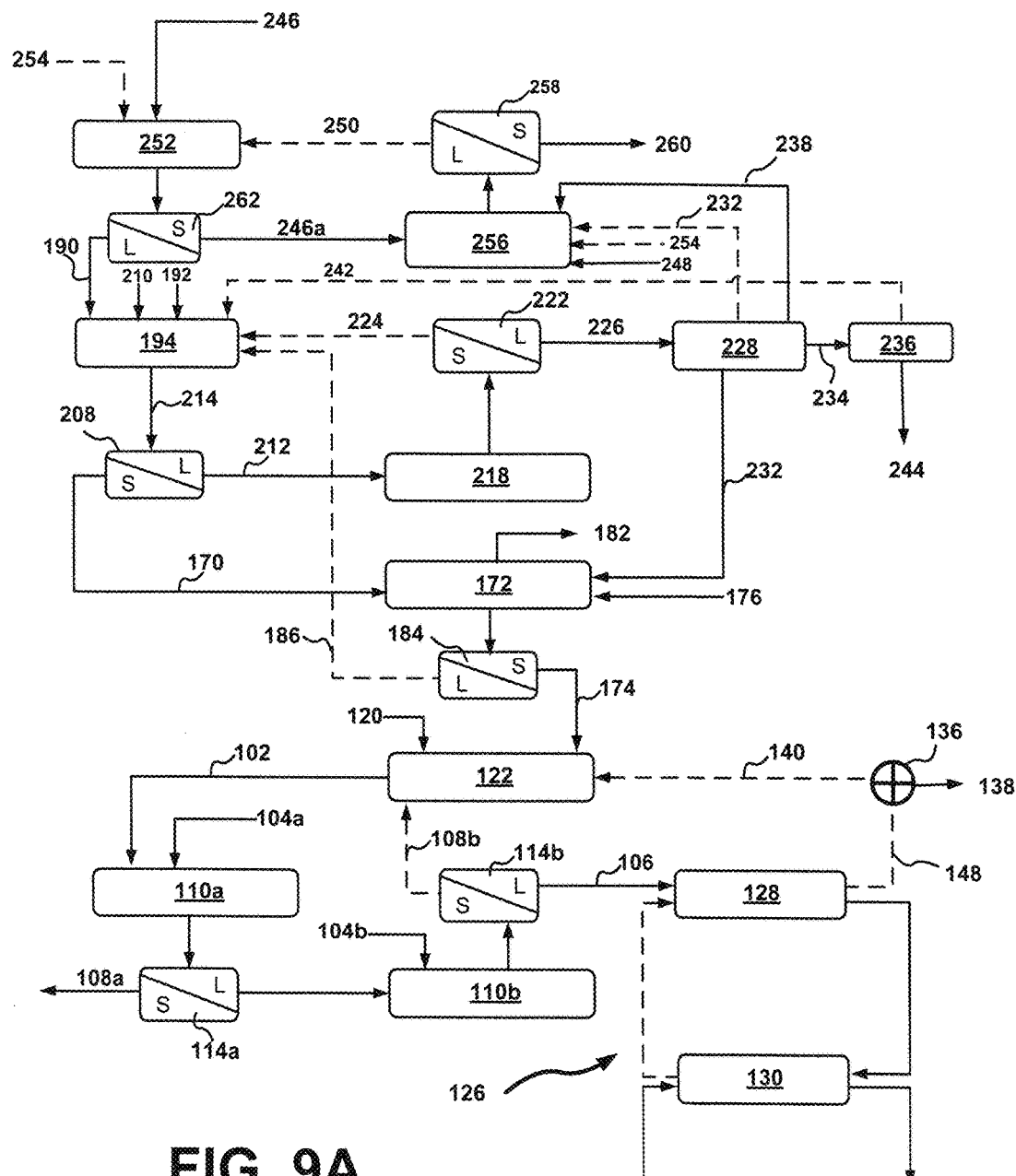
FIGS. 9A and 9B are flowsheets illustrating comprehensive methods for the extraction of rare earth elements from an ore incorporating various embodiments of the present disclosure.
Figure 9B:
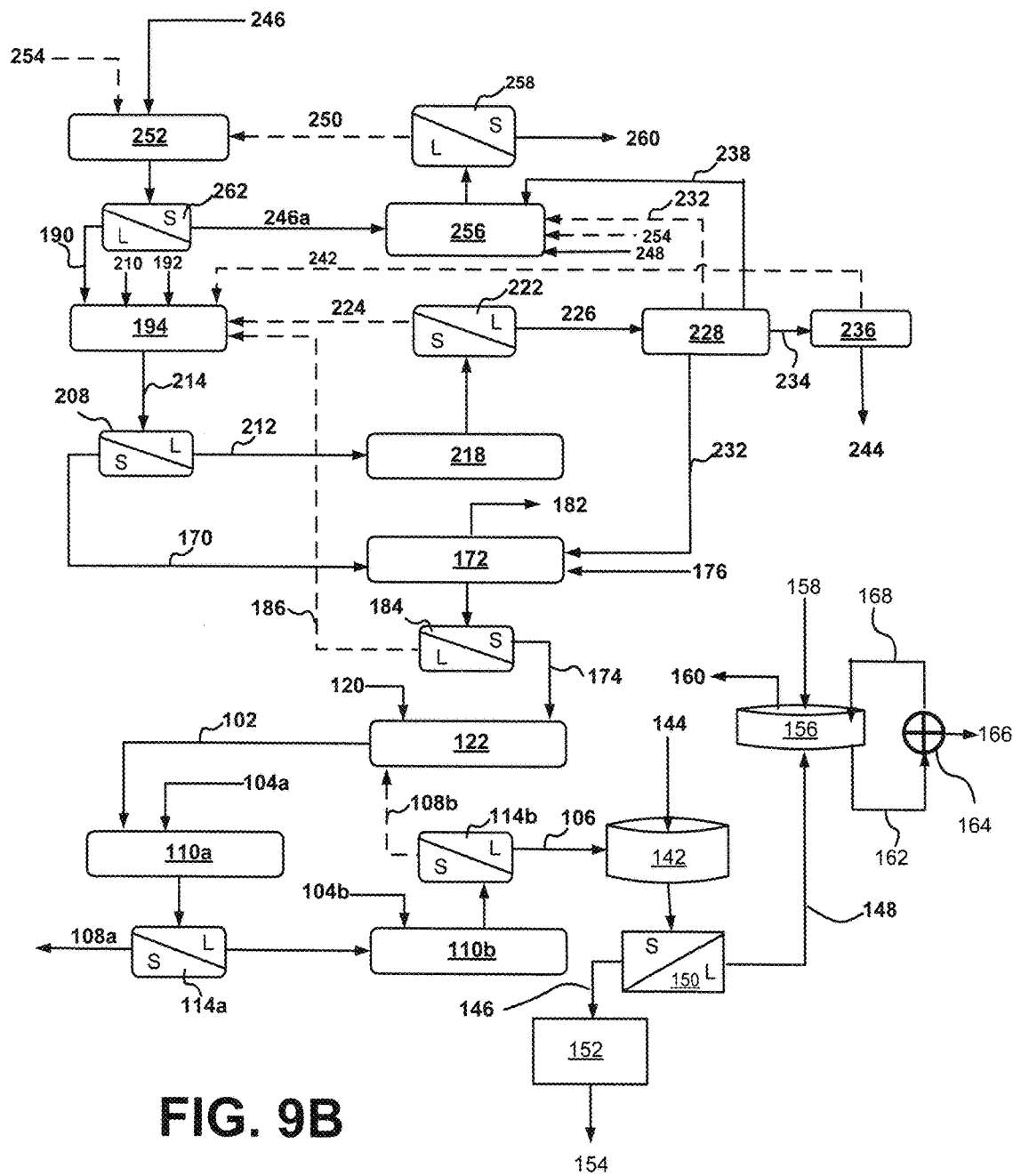

As is discussed above, it is an advantage of the methods disclosed herein that the final REE product is of very high purity, and includes low concentrations of non-REE elements such as base metals, uranium and thorium. Such a high purity REE product may be produced by combining the oxalate formation step described above with a metathesis step to convert the REE-oxalates to REE-carbonates, digesting the REE-carbonates in an acid and selectively precipitating thorium as thorium hydroxide from the solubilized REEs Comprehensive flowsheets incorporating various embodiments of the foregoing methods are illustrated in FIGS. 9A and 9B. In accordance with these flowsheets, a rare earth ore concentrate is leached in hydrochloric acid to form a pregnant liquor solution. Rare earth metals in the form of REE-oxalates are then precipitated from the pregnant liquor solution, and the REE-oxalates are then converted to REE-carbonates in a metathesis reaction. The REE-carbonate product, which also includes thorium carbonate, is then digested in nitric acid and the thorium is precipitated as thorium hydroxide by the addition of a hydroxide precipitant, leaving a nitrate solution that is rich in REEs and contains a very low concentration of other metals, including thorium, uranium and base metals. This nitrate solution can then be treated in a solvent extraction circuit to extract high purity rare earth metals (FIG. 9A), or can be treated to form REE-oxides (FIG. 9B).

Referring to both FIG. 9A and FIG. 9B, a rare earth ore concentrate 246 is subjected to a leaching circuit to form a PLS 190 substantially as described with respect to FIG. 8. The leaching process may include leaching a rare-earth ore concentrate 246 with an acid 248 such as HCl acid in a counter-current flow to enhance leaching efficiency and reduce acid consumption.

The concentrate 246 may be first contacted with recycled PLS 250 (e.g., containing HCl) in a pre-leaching step 252. In addition to the ore concentrate 246 and the recycled PLS 250, the pre-leaching step 252 may optionally include the addition of a reducing compound 254, for example a sulfur-containing compound such as sodium sulfite ($Na_2SO_3$) to precipitate barium (Ba) and/or radium (Ra), and/or to reduce $Fe^{3+}$ to $Fe^{2+}$ in the PLS 246. The pre-leaching step 252 is advantageously integrated (e.g., in counter-current flow) with a primary leaching step 256. As illustrated in FIGS. 9A and 9B, recycled HCl 238, e.g., recycled PLS from a subsequent distillation step 228 may be contacted with the incoming ore concentrate 246. In the primary leaching step 256, pre-leached ore concentrate 246a is contacted with additional acid 248 (e.g., HCl) to leach metals from the pre-leached ore concentrate 246a. A reducing compound 142 may also be used in the primary leaching step 256, as is described above with respect to pre-leaching step 252. The primary leaching step 256 may be carried out at an elevated temperature, such as at least about 40° C. to not greater than about 95° C., for a period of time and under conditions (e.g., agitation) sufficient to solubilize substantially all of the REEs (e.g., at least about 95 wt. % of the REEs) in the pre-leached ore concentrate 246a. In one particular example, the primary leaching step is carried out of a temperature of from about 50° C. to about 70° C. to reduce dissolution of barium. The use of lower leaching temperatures (e.g., about 50° C.) may also reduce the capital expense of the reactor by enabling fiberglass reactors to be utilized. In one characterization, the primary leaching step 256 is carried out for about 6 hours (e.g., for an average residence time of about 6 hours).

After primary leaching 256, a solid/liquid separation step 258 may be carried out to separate an acidic solution 250 comprising REEs from leach solids 260. The leach solids may be treated (e.g., with hydroxides or carbonates) to neutralize the leach solids 260 before disposal as tailings. The acidic solution 250 may be conveyed to the pre-leach step 252, after which the final PLS 190 is separated from the pre-leached ore concentrate 246a in a separation step 262, e.g., in a substantially continuous leaching circuit.

In addition to REEs, the PLS 190 may also include non-REE elements that are solubilized in the PLS 190, as is discussed above. It is a significant advantage of this embodiment that REE-oxalates may be precipitated from the PLS 190, while a substantial majority of the non-REE elements remain in solution, i.e., do not form oxalate compounds during the oxalate formation step. Particularly, very low concentrations of elements such as Al, Fe, Ca, Mg, n. P, Pb, S, Ti, U and/or Zn will precipitate with the REE-oxalates. As a result, the REE-oxalate product is of very high purity and a substantial proportion of the base metals and other metals such as uranium can be removed prior to extraction of the REEs, e.g., in a solvent extraction process.

After formation of the PLS 190, the PLS 190 is subjected to an oxalate formation step 194 where REEs and thorium are precipitated from the PLS 190, while a large proportion of other metals (e.g., base metals and uranium) advantageously remain in solution. The oxalate formation step 190 includes contacting the PLS 190 with oxalic acid 192 under conditions such that REE-oxalate compounds precipitate from the PLS 190. A sufficient amount of oxalic acid 192 is contacted with the PLS 190 to precipitate a majority of the REEs as REE-oxalates in an REE-oxalate product 170. Sodium oxalate ($Na_2C_2O_4$) 210 may also be contacted with the PLS 190 in the oxalate formation step 194, such as by adding the sodium oxalate 210 to the oxalic acid 192, or by adding the sodium oxalate 210 directly to the PLS 190. As is illustrated in FIGS. 9A and 9B, recycled sodium oxalate 224 may advantageously be input to the oxalate formation step 194 from a subsequent process step, such as from a thickening step 218 and separation step 222. Alternatively, or in addition to, fresh sodium oxalate 210 may be added to the oxalate formation step 194. In one example, the ratio of (fresh) oxalic acid 192 to sodium oxalate 210 may be greater than 1, and in one particular characterization, the ratio of oxalic acid 192 to sodium oxalate 210 may be at least about 3:1 and not greater than about 4:1, such about 3.5:1. As is noted above, the addition of recycled sodium oxalate 224 to the oxalate formation step 194 may advantageously reduce the total consumption of oxalic acid by the process, i.e., by the oxalate formation step 194. This reduction in oxalic acid consumption may represent a significant cost savings for the process.

As is described above with respect to FIG. 7, the oxalate formation step 194 may be carried out under conditions such that the formation of REE-oxalates is favored over the formation of most non-REE oxalates from the PLS 190. In one characterization, the oxalate formation step 194 may be carried out by maintaining a precipitation temperature for a sufficient amount of time to precipitate at least about 75 at. % of the REEs in the PLS 190 as particulate REE-oxalates such as, at least about 85 at. % of the REEs., at least about 90 at. % of the REEs, at least about 95 at. % of the REEs, or even at least about 98 at. %, at least about 99 at. % or 99.5 at. % of the REEs. In one example, the oxalate formation step 194 may be carried out for at least about 30 minutes and not greater than about 120 minutes, such as for about 60 minutes.

After formation of oxalate precipitates, the metal oxalate precipitates may be allowed to crystallize (e.g., to grow) over a period of time and the REE-oxalate product 170 may then be separated from an REE-depleted solution 212 in a separation step 208. For example, the mixture 214 may be allowed to cool over a period of time to allow crystallization of the metal oxalates to form the REE-oxalate product 170. Alternatively, the temperature of the reactants may be increased to a second crystallization temperature (e.g., greater than the first precipitation temperature) to enhance (e.g., to accelerate) crystallization and growth of the metal oxalate precipitates, particularly of the REE-oxalates. The crystallization of the oxalates may be carried out in the same reactor as the precipitation of the oxalates, or may be carried out in a separate reactor.

After crystallization, REE-oxalate product 170 may be separated from the REE-depleted solution 212 in a separation step 208. The REE-oxalate product 170 comprises predominately REE-metal oxalates and the REE-oxalate product 170 may be of very high purity. For example, the total non-REE metals (e.g., Ba, Na, K, Si, Sr and/or Th) may constitute not greater than about 5 wt. % of the REE oxalate product 170, such as not greater than about 3 wt. % or even not greater than 1 wt. %.

The REE-depleted solution 212 may be an acidic solution that includes solubilized metals that did not precipitate, e.g., to form a metal oxalate, during the oxalate formation step 194. For example, the REE-depleted solution 212 may include solubilized elements as listed in Table II above such as Fe, Mn, Th, U, F, Al, Ca, K, Mg, Na, Sr, Zn, P, S, Pb and Ti. The REE-depleted solution 212 may have high free acid content, and the free acid content may be higher than the free acid content of the PLS 190. As a result, the REE-depleted solution 212 may be recycled to conserve acid (e.g., HCl acid). As illustrated in FIGS. 9A and 9B, the REE-depleted solution 212 may be transferred to a thickening step 218. After thickening 218, a separation step 222 may be carried out to separate oxalates 224 (e.g., sodium oxalates), which then may be recycled to the oxalate formation step 194. The acidic solution 226 will contain a high concentration of chloride ions, and the solution 226 may be subjected to a distillation step 228 to recover water 232 and an acid 238. The water may be used as process water in other process steps, such as in a subsequent metathesis step 172, for filter washing etc. The 238 may also be recycled to other process steps such as a leaching step 252 and/or 256. As illustrated in FIGS. 9A and 9B, the acid is recycled to the pre-leaching step 252 in a closed loop. Residue 234 from the distillation may be further treated in a crystallization step 236 to recover and recycle additional oxalic acid crystals 242 to the oxalate formation step 194, further reducing the consumption of oxalic acid by the process. The by-product 244 from the crystallization step 236 contains metals, and may be processed to recover further metals of value, such as gold, uranium, aluminum, manganese, iron, magnesium, strontium and zinc.

The foregoing process steps described with respect to FIGS. 9A and 9B illustrate various ways that reagents (e.g., hydrochloric acid and oxalic acid) may be recycled within the process to significantly reduce reagent consumption and reduce operating expenses associated with the process.

As is described above with respect to FIGS. 5 and 6, the high purity REE-oxalate product 170 is converted in a metathesis step 172 to a REE-carbonate product 174 for subsequent dissolution of the REE-carbonate product 174 in an acid, e.g., to solubilize the REEs and thorium in an acid digestion step 122. In this embodiment, an REE-oxalate product 170 is contacted with a carbonate compound 176 such as sodium carbonate ($Na_2CO_3$) in the metathesis step 172, along with a solvent such as water (e.g., recycled water 232), which may be introduced with the other reactants or may be introduced separately. The only by-product of the metathesis step 172 is a high-purity carbon dioxide stream 182 which may be captured as a by-product.

In a separation step 184, the REE-carbonate product 174 (e.g., REE-carbonate particulates) may be separated from an oxalate solution 186 such as by using a filter 188. The oxalate solution 186 will include substantial amounts of dissolved oxalates (e.g., $Na_2C_2O_4 \cdot yH_2O$ when the carbonate compound 176 is sodium carbonate) and the oxalate solution 186 may advantageously be recycled back to the oxalate formation step 194 to further reduce the consumption of fresh reagents.

After formation of the high purity REE-carbonate product 174, the product 174 may be contacted with nitric acid 120 (e.g., fresh nitric acid or sulfuric acid) in an acid digestion step 122. The resulting acidic solution 102 may be an acidic solution substantially as described above with respect to FIGS. 1 and 2 above. The acidic solution 102 may then be contacted in a first hydroxylation step 110a with a hydroxide precipitant 104a to precipitate a thorium hydroxide product 108a from the acidic solution 102. The thorium hydroxide product 108a may be separated from the thorium depleted solution 106b in a separation step 114a. Thereafter, the intermediate thorium depleted solution 106b may be contacted in a second hydroxylation step 110b with a second hydroxide precipitant 104b to form the thorium depleted solution 106. The thorium depleted solution 106 may then separated from the second thorium hydroxide product 108b in a separation step 114b.

The amount of thorium hydroxide product 108b may be relatively small and there may be appreciable quantities of REEs in the thorium hydroxide product 108b. To reduce losses of REEs, the thorium hydroxide product 108b may advantageously be recycled back to the acid digestion step 122 where the thorium is re-digested with the REE-carbonate product 174. In this manner, all of the thorium hydroxide is removed from the acidic solution 102 with the first thorium hydroxide product 108a. When the thorium hydroxide product 108b is separated in separating step 114b, the resulting thorium depleted solution 106 is a relatively high purity RE-nitrate solution (or RE-sulfate solution in the event sulfuric acid is utilized in the digestion step 122).

Referring now to FIG. 9A, the high purity RE-nitrate solution 106 may then be subjected to a solvent extraction circuit 126 to extract REEs as metals from the thorium depleted solution 106. Having the REEs solubilized in nitrate media (nitric acid) may reduce the expenses associated with a solvent extraction circuit 126. The solvent extraction circuit 126 may include the steps of solvent extraction 128 and solvent stripping 130 with a stripping solvent 132. Because the thorium depleted solution 106 described herein is of extremely high purity, the solvent extraction circuit 126 may advantageously be operated at a reduced capital expense and reduced operating expense. The resulting products are very high purity and high value REE metals 134.

The thorium depleted solution 106 may also include substantial quantities of highly salable ammonium nitrate. Thus, an ammonium nitrate removal step 136 may be utilized to continuously or intermittently remove ammonium nitrate 138 from the solution 106. As illustrated in FIG. 9A, the ammonium nitrate is removed after the solvent extraction circuit 126, as the presence of ammonium nitrate in the thorium depleted solution 106 is not believed to impair the efficacy of the solvent extraction circuit 126. However, it will be appreciated that the ammonium nitrate separation step may also occur before the solvent extraction circuit 126 if desired.

The ammonium nitrate separation step 136 may include cooling the REE-depleted acidic solution 148 to a reduced temperature (e.g., below about 10° C.) to crystallize ammonium nitrate 138. Because ammonium nitrate 138 is highly soluble in acid, it may only be necessary to intermittently operate the separation step 136 to remove ammonium nitrate 138. Ammonium nitrate is valuable and salable by-product that is widely used in the fertilizer industry and may represent a significant source of revenue from the process. After separation of the ammonium nitrate 138 (intermittently or continuously), the resulting acid 140 (e.g., recycled nitric acid) may be recycled back to the process, e.g., back to the acid digestion step 122. Thus, the acid (e.g., input at 120) may be contained in an essentially "closed loop" within the process. Additional acid may be generated during the solvent extraction circuit due to cationic ion exchange releasing protons into solution. In this regard, a substantial quantity of the acid required for the acid digestion step may be provided by the recycled acid 140, and only a small amount of fresh acid 120 may be required for the process once steady state and continuous operations are achieved and maintained.

Referring now to FIG. 9B, an REE precipitation circuit replaces the solvent extraction circuit of FIG. 9A. Thus, the thorium depleted and REE-nitrate rich solution can be treated to precipitate high purity REE-compounds such as REE-oxides and/or REE-hydroxides which, for example, may be shipped to a separate facility for extraction of the REEs as metals. See FIG. 4 described above.

The thorium depleted solution 106 from the separation step 114b will typically have a pH in the range of about pH 3.6 to about pH 4 (e.g., about pH 3.8) and will be rich in REE-nitrates and may contain no, or extremely low levels of, thorium and/or uranium. This solution 106 is conveyed to an REE precipitation step 142, where the solution 106 is contacted with an REE precipitation agent 144, such as ammonium hydroxide, in sufficient quantities to increase the pH of the solution, such a by increasing the pH to at least about pH 4.5, such at least about ph 4.9. In one characterization, the pH during the precipitation step 144 is not greater than about pH 6 and may be about pH 5.5. At these pH levels, the REEs will precipitate from the solution 106 as REE-hydroxides 146, which may be separated from an REE-depleted nitrate solution 148 in a separation step 150.

The REE-hydroxides 146 may then be converted from the REE-hydroxides to REE-oxides. The REE-hydroxides 146 are conveyed to a drying step 152 where the REE-hydroxides are heated to a drying temperature that is sufficient to convert a substantial majority of the REE-hydroxides 146 to REE-oxides 154. In one example, the REE-hydroxides 146 are conveyed to a screw feed dryer for the substantially continuous production of the REE-oxides 154. In another example, the REE-hydroxides 146 may be stockpiled as necessary and dried batchwise.

It is an advantage of this embodiment that the resulting REE-oxide product 154 will have a very high purity, particularly with respect to base metals and radioactive metals such as uranium and thorium. In one example, the REE-oxide product 154 has a purity of at least about 98%, i.e., the REE-oxide product 154 comprises at least about 98% REE-oxides. Further, the REE-oxide product 154 may have a purity of at least about 99%, such as at least about 99.5%.

An REE-depleted nitrate solution 148 may also recovered from the separation step 158, and may have a high content of ammonium nitrate, such as from about 30 g/l to about 50 g/l ammonium nitrate. The solution 148 may be conveyed to a vessel 156 where ammonium hydroxide is stored for use in the process, i.e., where the recycled nitrate solution 148 is added to fresh ammonium hydroxide 158. An ammonium hydroxide product 160 such as an ammonium hydroxide solution may then be conveyed as needed to the process, e.g., to hydroxylation steps 110a/110b and/or to REE precipitation step 142. Because the recycled REE-depleted nitrate solution will contain ammonium nitrates, it may be desirable to remove the ammonium nitrates from the ammonium hydroxide vessel 156 on a continuous or intermittent basis. In this regard, a portion 162 of the solution contained within vessel 156 may be periodically bled off from the vessel 156 and subjected to an ammonium nitrate precipitation step 164 to crystallize an ammonium nitrate by-product 166 and recycle an ammonium nitrate depleted solution 168 back to the vessel 156. The ammonium nitrate by-product 166 will be of high purity and a valuable by-product of the process.

The flowsheets illustrated in FIGS. 9A and 9B may provide at least one or more of the following advantages.

The metathesis step produces a REE-carbonate product that is soluble in relatively dilute concentrations of acid, e.g., 6 wt. % or lower, as compared to other REE compounds such as REE-oxalates and REE-oxides. This results in a lower overall acid consumption and therefore reduced operating expense.

The metathesis advantageously removes uranium from the product, as uranium carbonate does not form during metathesis. In one example, at least about 95%, such as at least about 97% of the uranium contained in the pregnant liquor solution will be rejected in the during the metathesis step, leaving less than 5%, such as less than 3% of the initial uranium in the REE-carbonate product.

The metathesis step advantageously enables the oxalate reagents to be recycled back to the oxalate formation step, thereby reducing the consumption of fresh oxalic acid.

The resulting REE-nitrate solution is of extremely high purity, and contains extremely low quantities of radioactive elements such as radium, thorium and/or uranium. Essentially all radium may be removed with sulfites during leaching of the ore concentrate and subsequent oxalate formation steps. The bulk of the uranium is rejected at the oxalate formation step, and most remaining uranium is rejected during the metathesis step. Thorium is removed as thorium hydroxide when precipitated with a hydroxide precipitant. The REE-nitrate solution also is substantially free of suspended solids, such as silicate particulates, thereby substantially reducing crud or mud formation in the solvent extraction.

The REE-nitrate solutions may also reduce the capital expenses associated with the solvent extraction circuit as compared to other solutions such as REE-chloride solutions. For example, chloride solutions typically require titanium coated vessels to carry out the extraction. The use of a nitrate solution may eliminate this requirement.

The process may utilize several recycle streams and therefore is cost effective with respect to the reagents.

EXAMPLES

A pregnant liquor solution containing REEs is contacted with oxalic acid to precipitate metal oxalates. The precipitation temperature is about 70° C. No sulfite was added to the PLS, and therefore $Fe^{3+}$ was present. No recycle was performed. The concentration of oxalic acid is varied from 90 g/l to 115 g/l to 140 g/l to assess the effect of oxalic acid concentration on the purity of the precipitate product (i.e., the metal oxalates). Results are shown in Table III.

TABLE III

| Element | Oxalate @ 90 g/l $H_2C_2O_4$ (wt. %) | Oxalate @ 115 g/l $H_2C_2O_4$ (wt. %) | Oxalate @ 140 g/l $H_2C_2O_4$ (wt. %) |
|---|---|---|---|
| REEs[1] | | | |
| Ce | 16.511467 | 16.61625 | 16.36584 |
| La | 8.549287 | 8.323717 | 7.840823 |
| Nd | 5.490483 | 5.67714 | 5.908091 |
| Pr | 1.594311 | 1.635.82 | 1.66676 |
| Y | 0.075021 | 0.075069 | 0.7525 |
| TOTAL REEs | 32.220569 | 30.6922 | 32.534 |
| Impurity Elements | | | |
| Th | | 0.193692 | 0.218965 |
| U | 0.001687 | 0.001574 | 0.001865 |
| Si | 0.491763 | 0.46509 | 0.470356 |
| Au | <LOD | <LOD | 0.002628 |
| As | 0.002351 | 0.0011.58 | 0.002418 |
| Se | <LOD | <LOD | <LOD |
| Pb | <LOD | <LOD | <LOD |
| Zn | <LOD | <LOD | <LOD |
| Cu | 0.012393 | 0.012785 | 0.013937 |
| Ni | 0.032589 | 0.034371 | 0.03619 |
| Co | 0.071752 | 0.070868 | 0.070785 |
| Fe | 0.513656 | 0.530995 | 0.564361 |
| Mn | <LOD | <LOD | <LOD |
| Cr | <LOD | <LOD | <LOD |
| V | <LOD | <LOD | <LOD |
| Ti | <LOD | <LOD | <LOD |
| Ca | <LOD | <LOD | <LOD |
| K | <LOD | <LOD | <LOD |
| Zr | <LOD | <LOD | <LOD |
| Mo | 0.000372 | 0.000516 | 0.000781 |
| Nb | 0.000466 | 0.000678 | <LOD |
| Sr | 0.00376 | <LOD | <LOD |
| Mn | <LOD | <LOD | <LOD |
| Cr | <LOD | <LOD | <LOD |
| V | <LOD | <LOD | <LOD |
| Ti | <LOD | <LOD | <LOD |
| Ca | <LOD | <LOD | <LOD |
| K | <LOD | <LOD | <LOD |
| Al | <LOD | <LOD | <LOD |
| Mg | <LOD | <LOD | <LOD |
| Zr | <LOD | <LOD | <LOD |

[1]other REEs not analyzed
<LOD = below the limits of detection

As demonstrated by Table IV, REE-oxalates with a high proportion of REEs and a relatively low proportion of non-REEs can be obtained by oxalate precipitation over a range of oxalic acid concentrations, even at a precipitation temperature of about 70° C. In particular, it is noteworthy that many prior processes for separation of REEs from a pregnant liquor solution also precipitate many non-REE elements with the REEs, for example U, Si, As, Pb, Zn, Fe, Mn, Mo, Nb, Cr, Ti, Ca, K, Al and Zr.

In the following Example, thorium is precipitated from an acidic solution using a hydroxide precipitant at various pH levels to observe the effect of pH on the precipitation of thorium and of REES.

For these tests, 400 grams (326 ml) of a nitric acid solution having a free acid content of about 5 g/l and a specific gravity of 1.227 is added to a one liter vessel having a mixer. A 1M solution of ammonium hydroxide ($NH_4OH$) is added dropwise to the vessel until the target pH level is reached, and the target pH is maintained for one hour. A temperature of about 25° C. is maintained during the precipitation step. After 60 minutes, the vessel contents are filtered and the weight, specific gravity and free acid content of the filtrate are measured. The retentate is washed with deionized water and dried.

in the acidic solution may be precipitated as thorium hydroxide. When the pH is increased to pH 3.5, 95% of thorium is precipitated, however increasing amounts of REEs also begin to precipitate from the solution.

However, if thorium concentration in the solution is decreased, it is found that the pH can be increased without precipitating significant quantities of REEs from the solution. FIG. 10B illustrates the results of increasing the pH of a solution over a range from pH 3.0 to pH 3.8, where the initial thorium concentration is decreased to 117 mg/l. As is illustrated in FIG. 10B, pH levels at least as high as pH 3.8 can be utilized to extract a high percentage of the thorium without precipitating significant amounts of the REEs. The results for the tests at pH 3.5, pH 3.6 and pH 3.8 for a solution containing 117 mg/l thorium are given in Table V.

TABLE V

| Element | Feed Assay (mg/l or g/tonne) | Final Solution Assay pH 3.5 (mg/l or g/tonne) | Percent Removed @ pH 3.5 | Final Solution Assay @ pH 3.6 (mg/l or g/tonne) | Percent Removed @ pH 3.6 | Final Solution Assay @ pH 3.8 (mg/l or g/tonne) | Percent Removed @ pH 3.8 |
|---|---|---|---|---|---|---|---|
| La | 2710 | 2200 | 1 | 2220 | 0 | 2160 | 2 |
| Ce | 1870 | 1520 | 1 | 1540 | 0 | 1500 | 2 |
| Pr | 473 | 386 | 0 | 390 | 0 | 380 | 2 |
| Nd | 1630 | 1344 | 0 | 1364 | 0 | 1332 | 0 |
| Sm | 232 | 189 | 0 | 191 | 0 | 187 | 1 |
| Eu | 51.0 | 42 | 0 | 42 | 0 | 41 | 1 |
| Gd | 122 | 99 | 0 | 102 | 0 | 100 | 0 |
| Tb | 9.8 | 8 | 0 | 8 | 0 | 8 | 0 |
| Dy | 30.8 | 23 | 1 | 25 | 0 | 25 | 0 |
| Ho | 3.52 | 5 | 1 | 3 | 0 | 3 | 0 |
| Y | 74.4 | 60 | 1 | 61 | 0 | 59 | 3 |
| Er | 6.15 | 5.06 | 0 | 4.84 | 4 | 4.96 | 1 |
| Tm | 0.58 | 0.46 | 3 | 0.5 | 0 | 0.48 | 0 |
| Yb | 2.83 | 2.32 | 0 | 2.30 | 1 | 2.22 | 4 |
| Lu | 0.35 | 0.30 | 0 | 0.28 | 2 | 0.28 | 2 |
| Sc | 0.71 | 0.62 | 0 | 0.40 | 31 | 0.48 | 17 |
| Th | 117 | 69 | 28 | 65 | 32 | 51 | 46 |
| U | 0.22 | 0.18 | 0 | 0.18 | 0 | 0.18 | 0 |

TABLE IV

| Element | Acidic Solution Assay (mg/l or g/tonne) | % Precipitated @ pH 1.0 | % Precipitated @ pH 2.0 | % Precipitated @ pH 2.5 | % Precipitated @ pH 3.0 | % Precipitated @ pH 3.5 |
|---|---|---|---|---|---|---|
| La | 20000 | 7 | 5 | 4 | 0 | 2 |
| Ce | 13500 | 7 | 5 | 3 | 0 | 2 |
| Pr | 3150 | 3 | 0 | 7 | 0 | 19 |
| Nd | 11000 | 4 | 1 | 3 | 0 | 3 |
| Sm | 1580 | 4 | 0 | 8 | 0 | 19 |
| Eu | 352 | 3 | 0 | 7 | 0 | 19 |
| Gd | 814 | 2 | 0 | 5 | 0 | 15 |
| Tb | 62 | 3 | 0 | 8 | 4 | 22 |
| Dy | 204 | 2 | 0 | 5 | 0 | 17 |
| Ho | 24 | 2 | 0 | 4 | 1 | 19 |
| Y | 494 | 5 | 0 | 7 | 0 | 18 |
| Er | 40 | 3 | 0 | 7 | 0 | 15 |
| Tm | 4 | 4 | 4 | 3 | 0 | 18 |
| Yb | 19 | 7 | 6 | 5 | 2 | 21 |
| Lu | 3 | 5 | 5 | 5 | 2 | 21 |
| Sc | <5 | 0 | 0 | 3 | 22 | 70 |
| Th | 734 | 4 | 1 | 8 | 62 | 95 |
| U | 1 | 0 | 0 | 0 | 0 | 24 |

Figure 10A:
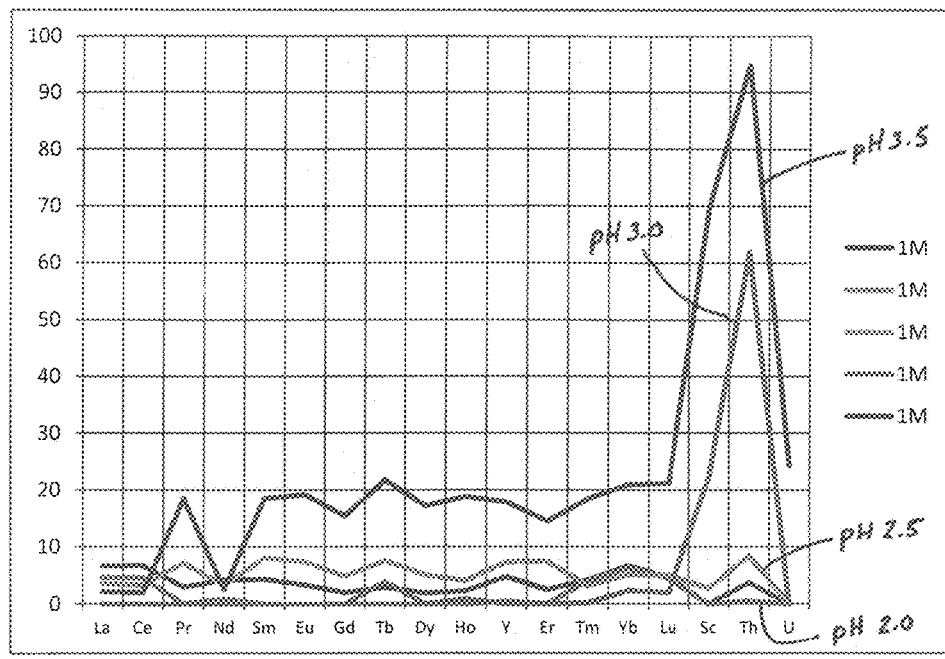
FIGS. 10A and 10B illustrate the effect of pH on selective thorium precipitation when using a hydroxide precipitant to precipitate thorium as thorium hydroxide.
Figure 10B:
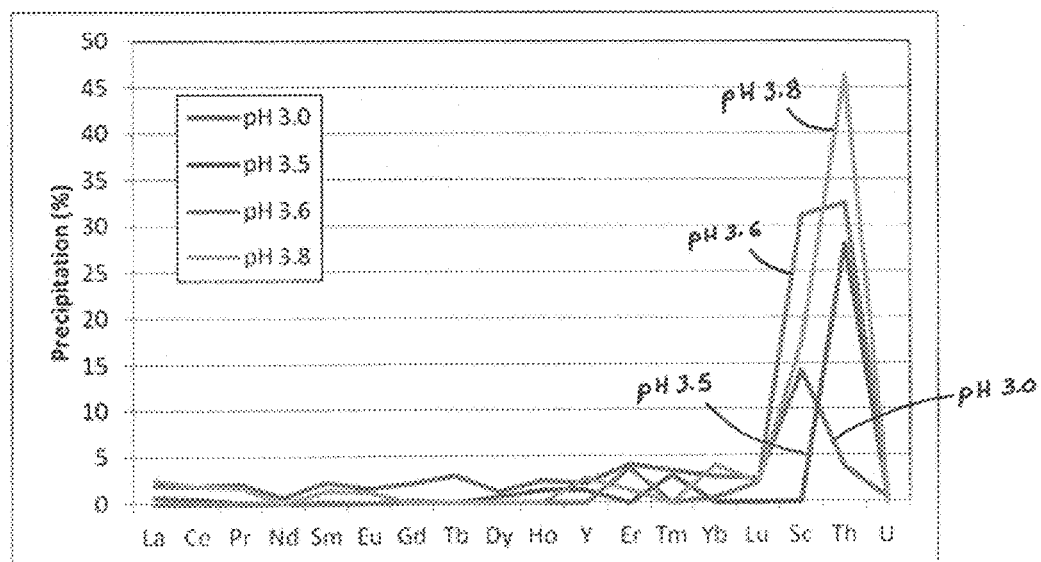

The foregoing data is graphically illustrated in FIG. 10A. This data demonstrates that at pH 3.0, 62% of the thorium As is illustrated in this Example, high levels of thorium can be extracted from a relatively dilute solution at increased pH levels, without extracting high levels of REEs from the solution.

While various embodiments have been described in detail, it is apparent that modifications and adaptations of those embodiments will occur to those skilled in the art. However, is to be expressly understood that such modifications and adaptations are within the spirit and scope of the present disclosure.

What is claimed is:

1. A method for the selective extraction of rare earth elements from base metals in a pregnant liquor solution, comprising the steps of:
    leaching a rare earth ore mineral concentrate derived from a mineral ore with HCl to form a pregnant liquor solution comprising at least chloride ions, solubilized rare earth elements and solubilized base metals, and comprising at least about 20 g/l iron;
    contacting the pregnant liquor solution comprising at least about 20 g/l iron with oxalic acid, where the pregnant liquor solution has a strength of at least about 0.5 M HCl;
    maintaining the pregnant liquor solution and the oxalic acid in contact at a first temperature to precipitate a metal oxalate product comprising REE-oxalate particulates from the pregnant liquor solution and form a mixture of the metal oxalate particulates in a REE-depleted solution; and separating the metal oxalate product from the REE-depleted solution, wherein at least about 97% of the total metallic elements in the metal oxalate product are rare earth elements.

2. The method recited in claim 1, further comprising the steps of:

recovering recyclable HCl from the REE-depleted solution; and recycling the recyclable HCl to the leaching step.

3. The method recited in claim 1, wherein the pregnant liquor solution comprises at least about 20 g/l REEs.

4. The method recited in claim 1, wherein the pregnant liquor solution comprises at least about 30 g/l REEs.

5. The method recited in claim 1, wherein the first temperature is at least about 80° C.

6. The method recited in claim 1, wherein the first temperature is not greater than about 90° C.

7. The method recited in claim 1, wherein the pregnant liquor solution and the oxalic acid are maintained in contact at the first temperature for a first period of time sufficient to precipitate at least about 90 at. % of the REEs from the pregnant liquor solution as REE-oxalates.

8. The method recited in claim 1, comprising the steps of:

after the maintaining at a first temperature, increasing the temperature of the mixture to a second temperature that is greater than the first temperature; and maintaining the mixture at the second temperature to crystallize the REE-oxalate particulates.

9. The method recited in claim 8, wherein the second temperature is at least about 5° C. greater than the first temperature.

10. The method recited in claim 8, wherein the second temperature is at least about 90° C.

11. The method recited in claim 8, wherein the second temperature is not greater than about 98° C.

12. The method recited in claim 1, wherein the contacting step comprises contacting the pregnant liquor solution with oxalic acid and sodium oxalate.

13. The method recited in claim 1, wherein the pregnant liquor solution further comprises actinide elements.

14. The method recited in claim 1, further comprising the step of:

subjecting the metal oxalate product to a metathesis step to convert the metal oxalates to metal carbonates.

15. A method for the selective extraction of rare earth elements from base metals in a pregnant liquor solution, comprising the steps of:

leaching a rare earth ore mineral concentrate derived from a mineral ore with HCl to form the pregnant liquor solution, the pregnant liquor solution comprising at least solubilized rare earth elements and solubilized base metals;

contacting the pregnant liquor solution with oxalic acid;

maintaining the pregnant liquor solution and the oxalic acid in contact at a first temperature of at least about 80° C. to precipitate a metal oxalate product comprising REE-oxalate particulates from the pregnant liquor solution and form a mixture of the metal oxalate particulates in a REE-depleted solution;

after the maintaining at a first temperature, increasing the temperature of the mixture to a second temperature that is at least about 5° C. greater than the first temperature;

maintaining the mixture at the second temperature to crystallize the REE-oxalate particulates; and separating the metal oxalate product comprising the crystallized REE-oxalate particulates from the REE-depleted solution;

wherein at least about 97% of the total metallic elements in the metal oxalate product are rare earth elements.

16. The method recited in claim 15, wherein the pregnant liquor solution has a strength of at least about 0.5M HCl.

17. The method recited in claim 15, wherein the pregnant liquor solution comprises at least about 30 g/l REEs.

18. The method recited in claim 15, wherein the pregnant liquor solution comprises at least about 20 g/l iron (Fe).

19. The method recited in claim 15, wherein the second temperature is at least about 90° C.

* * * * *